(12) United States Patent
Murashita

(10) Patent No.: US 7,247,148 B2
(45) Date of Patent: Jul. 24, 2007

(54) PROTECTOR AND STORAGE NEEDLE ASSEMBLY

(75) Inventor: Takato Murashita, Yamanashi (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 749 days.

(21) Appl. No.: 10/450,809

(22) PCT Filed: Dec. 5, 2001

(86) PCT No.: PCT/JP01/10625

§ 371 (c)(1),
(2), (4) Date: Jun. 18, 2003

(87) PCT Pub. No.: WO02/49696

PCT Pub. Date: Jun. 27, 2002

(65) Prior Publication Data

US 2004/0049163 A1    Mar. 11, 2004

(30) Foreign Application Priority Data

Dec. 18, 2000 (JP) ............................. 2000-384370
Mar. 29, 2001 (JP) ............................. 2001-097558

(51) Int. Cl.
*A61M 5/00* (2006.01)
(52) U.S. Cl. ................... 604/110; 604/198; 604/164.08
(58) Field of Classification Search ................ 604/263, 604/192, 197, 198, 164.08, 110; 128/919
See application file for complete search history.

(56) References Cited

U.S. PATENT DOCUMENTS 5,322,517 A    6/1994  Sircom et al.
5,882,337 A *  3/1999  Bogert et al. ................ 604/110
6,117,108 A    9/2000  Woehr et al.
2004/0049155 A1 * 3/2004 Schramm ..................... 604/110

FOREIGN PATENT DOCUMENTS

| CN | 1267226 A | 9/2000 |
| EP | 0 750 918 A2 | 1/1997 |
| WO | WO 99/08742 A1 | 2/1999 |

\* cited by examiner

*Primary Examiner*—Nicholas Lucchesi
*Assistant Examiner*—Theodore J. Stigell
(74) *Attorney, Agent, or Firm*—Buchanan Ingersoll & Rooney PC

(57) ABSTRACT

The present invention provides a protector and an indwelling needle assembly which are capable of accommodating a needle tip of a used needle body by a simple operation to ensure a high level of safety during needle disposal or the like.

Provided is a protector displaceable between a first attitude in which the protector can move relatively along a longitudinal direction of a needle body having a sharp needle tip at its tip end and a second attitude in which the relative movement of the protector along the longitudinal direction of the needle body is prohibited in a state where the protector covers the needle tip of the needle body, the protector having a plate-like brake portion having formed therein a hole through which the needle body can penetrate, characterized in that, in the second attitude, an inclination angle of the brake portion relative to the needle body becomes smaller than the inclination angle in the first attitude, so that a frictional force is generated or increased between an inner surface of the hole of the brake portion and an outer peripheral surface of the needle body to thereby prohibit the relative movement of the protector along the longitudinal direction of the needle body.

7 Claims, 15 Drawing Sheets

PROTECTOR AND STORAGE NEEDLE ASSEMBLY

FIELD OF THE INVENTION

The present invention relates to a protector and an indwelling needle assembly. More specifically, the invention relates to a protector for a needle body that is used, for example, by being punctured into a blood vessel etc during infusion or blood collection, and to an indwelling needle assembly provided with the protector.

DESCRIPTION OF PRIOR ART

When performing an infusion to a patient, an indwelling needle to be connected with an infusion line is punctured into a blood vessel of the patient to be indwelled therein. Such an indwelling needle consists of a hollow outer needle, an outer needle hub secured to the base end of the outer needle, an inner needle inserted into the outer needle and having a sharp needle tip at its tip end, and an inner needle hub secured to the base end of the inner needle.

When puncturing the indwelling needle into the blood vessel of the patient, the inner needle is inserted into the outer needle and then the puncturing operation is performed in a state where the needle tip of the inner needle is being projected through the tip end of the outer needle. Then, when the needle tip of the inner needle reaches the interior of the blood vessel, blood flowing in through an opening at the needle tip passes through the inner hole of the inner needle to flow into the interior of the inner needle hub that is transparent (flashback). Thus, it can be confirmed that the inner needle has secured the blood vessel.

Upon confirming this flashback, the inner needle and the outer needle are advanced slightly to insert the tip end of the outer needle into the blood vessel. Next, while grasping the outer needle with a hand, the inner needle is drawn out from the outer needle and the connector of the infusion line is connected to the outer needle hub. Then, the administration of infusion is performed via the connected infusion line and the outer needle.

In this case, the inner needle drawn out from the outer needle becomes unnecessary, so that it is discarded for disposal. However, if it is disposed of as it is, there is a fear that a finger etc of a person performing the disposal or the like is accidentally stuck with the needle tip of the inner needle. In particular, since blood is adhered to or remains on the surface of the inner needle or its interior, such accidental needle sticks could become the cause of infection.

Accordingly, it is preferred that a used inner needle be accommodated into a hard, sturdy dedicated container for disposal so as to prevent accidental sticking of the needle tip. However, from the viewpoint of efficiency of operations, it is difficult to carry such a dedicated container at all times and bring it to each patient. Therefore, under the present circumstances, such measures are taken as to dispose of a used inner needle by putting it into an unsealed packing material that previously accommodated the indwelling needle kit, or discard it by covering a cap over its needle tip.

However, when performing such an operation of packing the inner needle in a packing material or covering it with the cap, too, utmost caution needs to be exercised so that a hand of the operator is not accidentally stuck with the needle tip of the inner needle, thus causing a problem in that a great deal of time and trouble is required for the disposal of a used inner needle.

An object of the present invention is to provide a protector capable of accommodating the needle tip of a used needle body by a simple operation to ensure a high level of safety during needle disposal or the like, and to provide an indwelling needle assembly provided with the protector.

SUMMARY OF THE INVENTION

The above object can be attained by the present invention as described in (1) to (25) below.

(1) A protector displaceable between a first attitude in which the protector can move relatively along a longitudinal direction of a needle body having a sharp needle tip at its tip end and a second attitude in which the relative movement of the protector along the longitudinal direction of the needle body is prohibited in a state where the protector covers the needle tip of the needle body, the protector having a plate-like brake portion having formed therein a hole through which the needle body can penetrate, characterized in that, in the second attitude, an inclination angle of the brake portion relative to the needle body becomes smaller than the inclination angle in the first attitude, so that a frictional force is generated or increased between an inner surface of the hole of the brake portion and an outer peripheral surface of the needle body to thereby prohibit the relative movement of the protector along the longitudinal direction of the needle body.

(2) The protector according to (1) described above, having:

urging means for urging the brake portion so that the inclination angle of the brake portion relative to the needle body becomes smaller; and inclination regulating means for regulating an inclination of the brake portion relative to the needle body in the first attitude, in which the regulation of the inclination effected by the inclination regulating means is released upon movement of the protector to a tip end portion of the needle body to thereby bring the protector into the second attitude from the first attitude.

(3) A protector displaceable between a first attitude in which the protector can move relatively along a longitudinal direction of a needle body having a sharp needle tip at its tip end and a second attitude in which the relative movement of the protector along the longitudinal direction of the needle body is prohibited in a state where the protector covers the needle tip of the needle body, the protector having a main body portion formed by deforming a plate-like member having an elasticity, characterized in that:

a first hole and a second hole through which the needle body can penetrate are formed in the main body portion;

a penetration portion through which the needle body can penetrate is formed on the needle tip side of the main body portion;

in the first attitude, the needle body penetrates through the first hole, the second hole, and the penetration portion, and by moving the protector in a tip end direction relative to the needle body from that state to release an engagement between the penetration portion and the needle body, the protector is elastically deformed into the second attitude such that an inclination angle of the plate-like member near the first hole relative to the needle body becomes smaller than the inclination angle in the first attitude, so that a frictional force is generated or increased between an inner surface of the first hole and an outer peripheral surface of the needle body to thereby prohibit the relative movement of the protector along the longitudinal direction of the needle body.

(4) The protector according to (3) described above, in which the tip end portion of the main body portion covers the needle tip of the needle body in the second attitude.

(5) The protector according to (3) or (4) described above, in which the main body portion has a substantially S shape as a whole, the first hole is formed in the center of the main body portion, and the second hole is formed on the needle root side of the main body portion.

(6) The protector according to any one of (3) through (5) described above, having a lateral displacement preventing member which is located between the penetration portion and the first hole and prevents lateral displacement of the needle tip of the needle body in the second attitude.

(7) The protector according to any one of (3) through (6) described above, having a cap member which is located between the penetration portion and the first hole and covers the needle tip of the needle body in the second attitude.

(8) The protector according to any one of (1) through (7) described above, having means for exerting such a force on the brake portion or the plate-like member near the first hole as to make the inclination angle thereof become smaller upon pressing the tip end portion of the protector in a base end direction in the second attitude.

(9) The protector according to any one of (1) through (8) described above, in which, in the first attitude, the inclination angle of the brake portion or the plate-like member near the first hole relative to the needle body is substantially a right angle.

(10) The protector according to any one of (1) through (9) described above, in which an inner diameter of the first hole (the hole) is 0.01 to 1 mm larger than an outer diameter of the needle body.

(11) The protector according to any one of (1) through (10) described above, in which a thickness of the brake portion or the plate-like member is 0.05 to 2 mm.

(12) A protector displaceable between a first attitude in which the protector can move relatively along a longitudinal direction of a needle body having a sharp needle tip at its tip end and a second attitude in which the relative movement of the protector along the longitudinal direction of the needle body is prohibited in a state where the protector covers the needle tip of the needle body, the protector including:

a plate-like brake portion constructed of a metallic material and having formed therein a hole through which the needle body can penetrate;

urging means for urging the brake portion so as to make an inclination angle of the brake portion relative to the needle body become smaller; and needle-body abutting portion constructed of a resin material, which is provided further on the needle tip side than the brake portion and has a function of abutting with the needle body in the first attitude to prevent the inclination angle of the brake portion relative to the needle body from changing, characterized in that, when the protector is moved in a tip end direction from the first attitude relative to the needle body and the needle-body abutting portion passes the needle tip to be separated apart from the needle body, the protector is deformed into the second attitude such that the inclination angle of the brake portion relative to the needle body becomes smaller than the inclination angle in the first attitude due to the urging means, so that a frictional force is generated or increased between an inner surface of the hole and a surface of the needle body to thereby prohibit the relative movement of the protector along the longitudinal direction of the needle body.

(13) The protector according to (12) described above, in which the urging means is a plate-like member extending continuously from the brake portion and exerts an urging force due to its elasticity.

(14) The protector according to (12) or (13) described above, in which, in the first attitude, a sliding resistance of the needle-body abutting portion with respect to the needle body is smaller than a sliding resistance of the brake portion with respect to the needle body.

(15) The protector according to any one of (12) through (14) described above, having a needle-tip receiving portion that covers the needle tip from the tip end side.

(16) The protector according to any one of (12) through (15) described above, having a cover portion that covers at least an area near the needle-body abutting portion, the cover portion having a function of hindering an operation of moving the area near the needle-body abutting portion in a tip end direction in the second attitude.

(17) The protector according to any one of (12) through (16) described above, in which a second hole through which the needle body can penetrate is formed further on the needle root side than the brake portion.

(18) The protector according to (17) described above, having a cover portion which is provided continuously from a member near the second hole and covers at least the area near the needle-body abutting portion, in which, when an external force acting in a base end direction and/or a tip end direction is imparted to the cover portion in the second attitude, such a force as to make an inclination angle of the member near the second hole relative to the needle body become smaller is exerted on the member near the second hole.

(19) The protector according to any one of (12) through (18) described above, in which the protector covers the needle tip of the needle body substantially from all around in the second attitude.

(20) An indwelling needle assembly characterized by including:

an inner needle having a sharp needle tip at its tip end;

the protector according to any one of (1) through (19) described above which is fitted to the inner needle;

an inner needle hub installed on the base end side of the inner needle;

a hollow outer needle into which the inner needle can be inserted; and an outer needle hub installed on the base end side of the outer needle.

(21) The indwelling needle assembly according to (20) described above, having connecting means for connecting the outer needle hub and the protector with each other.

(22) The indwelling needle assembly according to (21) described above, in which:

when the inner needle hub is moved in a base end direction relative to the outer needle hub, a connected state between the protector and the outer needle with hub is maintained by the connecting means until the protector is displaced from the first attitude into the second attitude by being moved in a tip end direction relative to the inner needle; and the protector and the outer needle hub can be separated from each other after the protector is displaced into the second attitude.

(23) The indwelling needle assembly according to (21) or (22) described above, in which the connecting means has a rupturing portion that ruptures upon the separation of the protector and the outer needle hub from each other.

(24) The indwelling needle assembly according to any one of (21) through (23) described above, in which the connecting means has an abutting member that abuts with the protector from the base end side.

According to the present invention, there can be provided a protector and an indwelling needle assembly which ensure an excellent level of hygiene and safety by allowing a used needle body to be swiftly and safely covered with the protector by a simple operation and eliminating accidental sticking of the needle tip into a hand, finger, etc during needle disposal or the like.

Further, according to the present invention, the above-mentioned effect can be realized using an extremely small protector, and during its use, the protector can be accommodated in a slight space provided in the needle root portion. Therefore, it is easy to secure the installation space for the protector, so that the protector can be used by being fitted to an ordinary needle body that does not have a special structure.

Further, the protector of the present invention, which has the needle-body abutting portion constructed of a resin material, can be moved relative to the needle body smoothly (with a relatively small operational force) in the first attitude. Thus, the operation of covering the needle tip with the protector can be performed in a swift, easy, and reliable manner.

Further, if the main body portion of the protector is formed by deforming the plate-like member, the above-mentioned effect can be attained by using an extremely simple structure.

Further, if the lateral displacement preventing member is provided, it is possible to more reliably prevent the needle tip from projecting even if a strong, external force in a lateral direction is exerted on the protector.

Further, according to the indwelling needle assembly of the present invention, it is unnecessary to perform machining (such as forming a concave portion or a convex portion) on the inner needle (needle body) to prevent dislodging of the protector therefrom. As a result, the tip end portion of the inner needle can be formed to have a smooth outer peripheral surface, thereby facilitating manufacture while not causing a reduction in the strength of the inner needle or an increase in insertion resistance.

Further, if the connecting means is provided in the indwelling needle assembly of the present invention, the needle tip of the inner needle can be covered with the protector more reliably by a simpler operation, thus achieving a further improvement in safety and operability.

DESCRIPTION OF THE PREFERRED EMBODIMENT MODES

Hereinbelow, a protector of the present invention will be described in detail based on preferred embodiment modes thereof shown in the accompanying drawings.

First Embodiment of Protector

Figure 1:
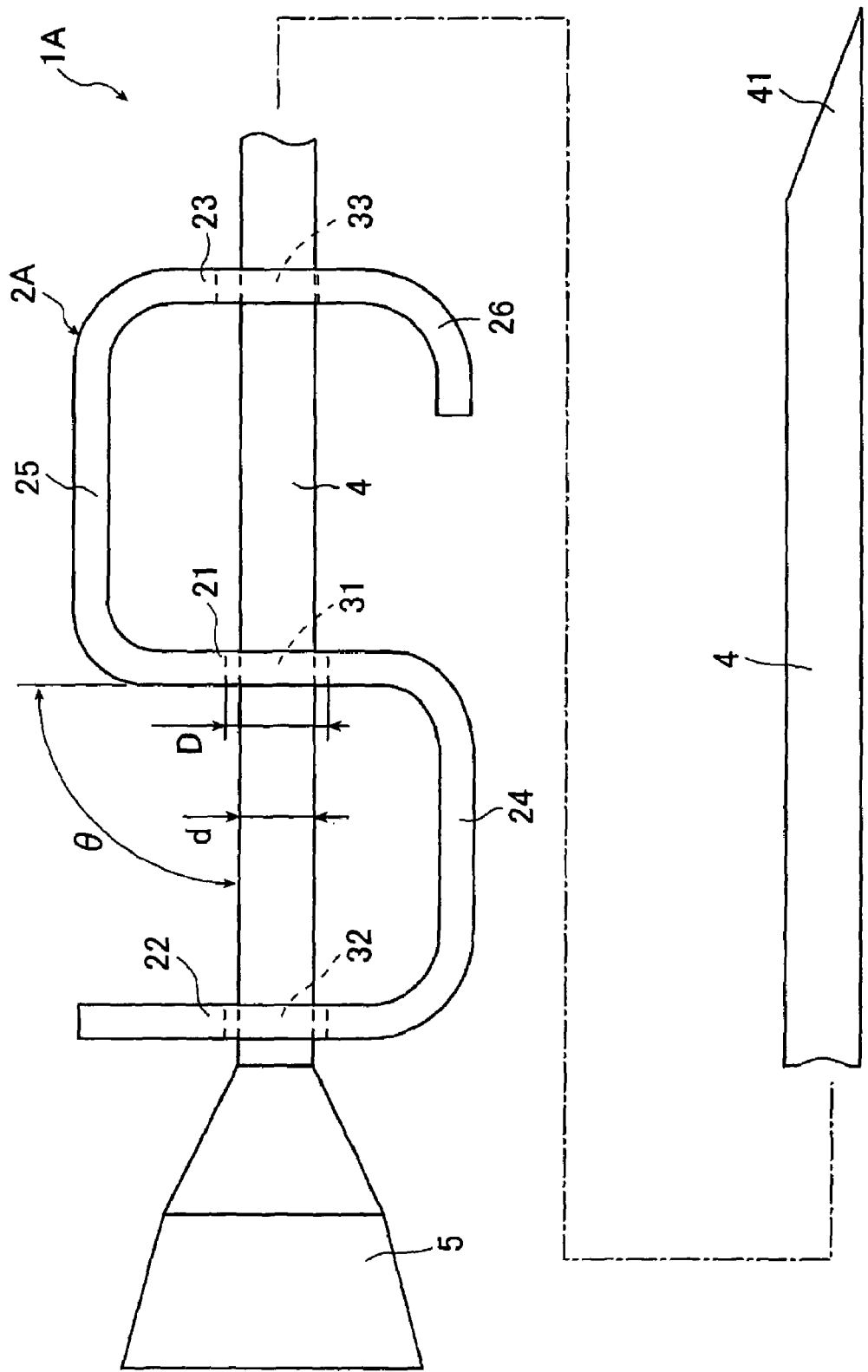
FIG. 1 is a side view (use state) showing a puncturing instrument (injection needle) having a protector according to a first embodiment of the present invention.
Figure 2:
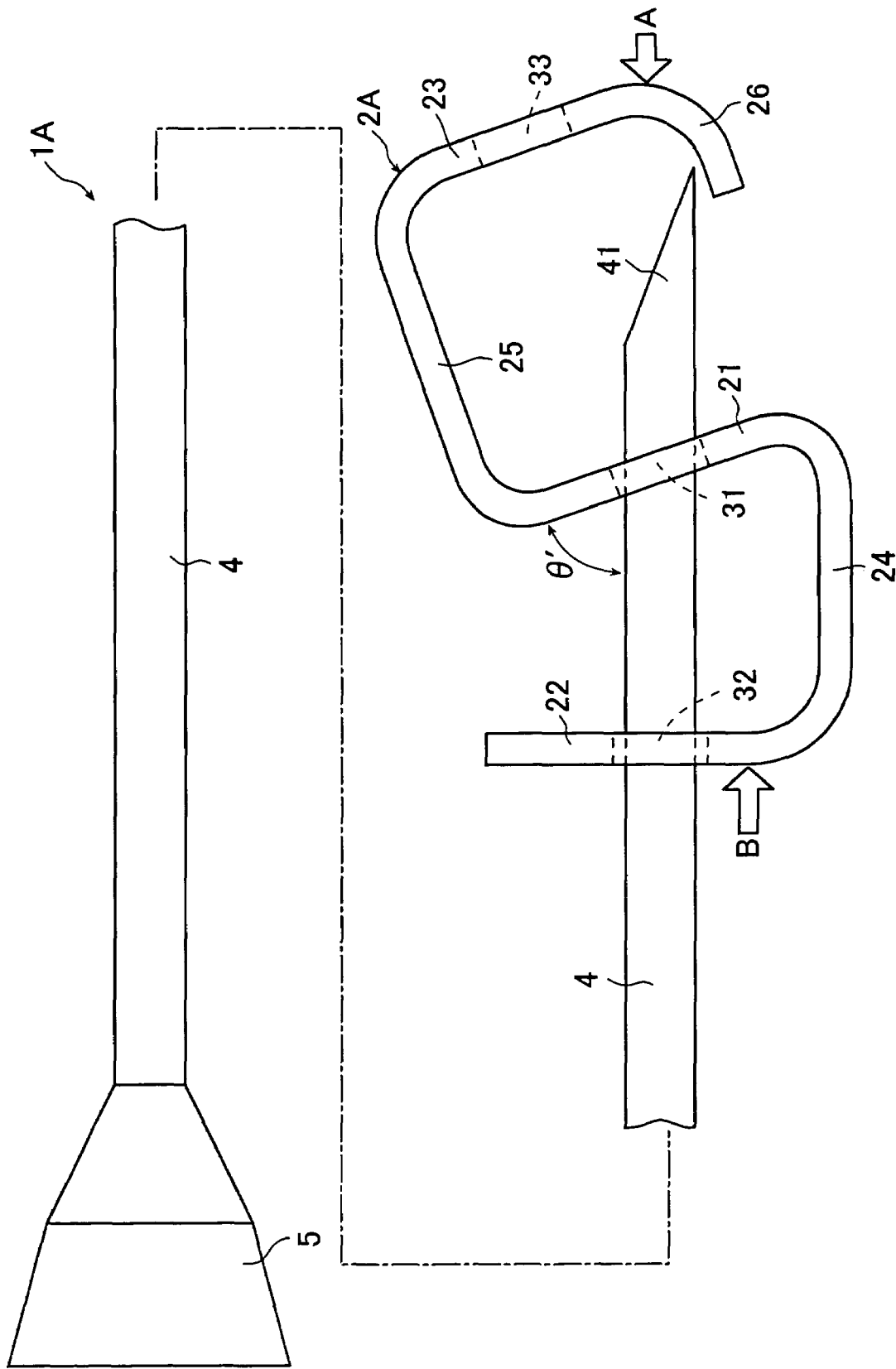
FIG. 2 is a side view (needle-tip accommodating state) showing the puncturing instrument (injection needle) having the protector according to the first embodiment of the present invention.

FIGS. 1 and 2 are each a side view showing a protector according to a first embodiment of the present invention. Note that, in the following description, the needle tip side as seen in FIGS. 1 and 2 is referred to as a "tip end", whereas the hub side is referred to as a "base end". Also, with the tip end being pointed up, the left-hand side is referred to as "one end", whereas the right-hand side is referred to as "the other end".

A puncturing instrument 1A shown in FIGS. 1 and 2 is provided with a needle tube (needle body) 4 having a sharp needle tip 41 at its tip end, a protector 2A which is mounted to the needle tube 4 and is capable of accommodating the needle tip 41 of the needle tube 4, and a hub 5 fixed to the base end of the needle tube 4. Hereinbelow, a description will be given of the constructions of the respective portions.

The needle tube 4 is a hollow needle, which is constructed of, for example, a metallic material such as stainless steel, aluminum or aluminum alloy, or titan or titan alloy. The sharp needle tip 41 is formed at the tip end portion of the needle tube 4. The shape of the needle tip 41 is not particularly limited; in the present embodiment, the needle tip 41 is shaped so as to have an edge surface that is inclined at a predetermined angle relative to the longitudinal axis of the needle tube 4.

The hub 5 is secured (fixed) in a liquid-tight manner to the base end of the needle tube 4, so that the inner hole of the needle tube 4 communicates with the inner portion of the hub 5.

Examples of the method for securing the needle tube 4 to the hub 5 include caulking, fusing (thermal fusing, high-frequency fusing etc), and adhesion using an adhesive.

The hub 5 consists of a substantially tubular member, and is preferably constructed of a transparent (uncolored transparent), colored transparent, or semi-transparent resin to ensure the visibility of its inner portion.

The hub 5 has a tapered shape such that its outer and inner diameters gradually increase toward the base end thereof. Into the thus tapered portion, for example, the tip end portion of a syringe (not shown) is inserted, thereby fitting the puncturing instrument 1A to the syringe.

The constituent material for the hub 5 is not particularly limited, and examples thereof may include polyolefins such as polyethylene, polypropylene, polybutadiene, and an ethylene/vinyl acetate copolymer, polyvinyl chloride, polyurethane, polystyrene, polymethyl methacrylate, polycarbonate, polyamide, polyesters such as polyethylene terephthalate, and polybutylene terephthalate, and various types of resin materials such as acrylic resins, ABS resin, AS resin, ionomer, polyacetal, polyphenylene sulfide, and polyetheretherketone.

The protector 2A is formed by deforming (bending) a plate-like member having an elasticity. The protector 2A has a first area (brake portion) 21 located at substantially the longitudinal center, a second area 22 located on the needle root side (base end side), a third area 23 located on the needle tip side (tip end side), a rear connection portion 24 connecting the other end of the first area 21 and the other end of the second area 22 with each other, and a front connection portion 25 connecting the one end of the first area 21 and the one end of the third area 23 with each other. Thus, the protector 2A has a substantially S shape as a whole.

Provided in the first area 21 of the protector 2A is a first hole 31 having a substantially round shape, provided in the second area 22 is a second hole 32, and provided in the third area 23 is a third hole 33. The first hole 31, the second hole 32, and the third hole 33 are holes through which the needle tube 4 can be penetrated.

Further, according to the construction shown in the figure, an inwardly curved (bent) cover portion 26 is provided at the other end of the third area 23.

During use of the puncturing instrument 1A (when it is punctured into a living body or the like), the protector 2A described above assumes an attitude shown in FIG. 1, that is, an attitude in which the needle tube 4 is penetrated through (inserted) through the first hole 31, the second hole 32, and the third hole 33 (hereinafter, this attitude is referred to as the "first attitude"). In this first attitude, the protector 2A is capable of moving in a longitudinal direction relative to the needle tube 4. Normally, as shown in FIG. 1, the puncturing instrument 1A is used in a state where the protector 2A is located at the base end of the needle tube 4 (hereinafter, this state is referred to as the "use state").

According to the construction shown in the figure, in the first attitude, the first area 21, the second area 22, and the third area 23 are each substantially perpendicular to the needle tube 4, and the rear connection portion 24 and the front connection portion 25 are each substantially parallel to the needle tube 4. As a result, in the first attitude, the angle formed between the first area 21 and the rear connection portion 24 is a substantially right angle.

On the other hand, in a natural state (a state where no external force is imparted) where the protector 2A is not fitted to the needle tube 4 and thus no external force is exerted thereon, the angle formed between the first area 21 and the rear connection portion 24 is set to be smaller than that obtained in the state shown in FIG. 2. That is, the protector 2A is fitted to the needle tube 4 while being subjected to deformation (elastic deformation) such that the first area 21 and the rear connection portion 24 are spread apart from each other.

Due to such deformation, in the state when the protector 2A is being fitted to the needle tube 4, the first area 21 is urged in such a direction as to make the inclination angle thereof relative to the needle tube 4 (the angle indicated by $\theta$ in FIG. 1 and by $\theta'$ in FIG. 2) become smaller. In other words, due to its elasticity, the portion of the protector 2A between the first area 21 and the rear connection portion 24 serves as urging means for urging the first area 21 in such a direction as to make the inclination angle of the first area 21 relative to the needle tube 4 become smaller.

In this case, the inclination angle of the first area 21 relative to the needle tube 4 can be represented by two values depending on which side of the angle formed by the first area 21 and the needle tube 4 is selected as a reference. In this specification, the "inclination angle of the first area 21 relative to the needle tube 4" refers to the angle that is less than 90 degrees (the smaller angle) at the condition of a second attitude described later. That is, in this embodiment, it refers to the angle indicated by $\theta$ in FIG. 1 and by $\theta'$ in FIG. 2. This angle will be hereinafter referred to as the "first-area inclination angle".

In the first attitude shown in FIG. 1, the needle tube 4 penetrates through the third hole 33 formed in the third area 23, which serves to inhibit the protector 2A from being deformed in such a way that the first-area inclination angle becomes smaller due to the urging force of the urging means. As a result, as described above, the first-area inclination angle $\theta$ in the first attitude is kept at a substantially right angle. In other words, the third hole 33 serves as inclination regulating means for regulating the first-area inclination angle $\theta$ to be a substantially right angle by engaging with the needle tube 4 in the first attitude.

Note that, the above-mentioned inclination regulating means according to this embodiment is not limited to the third hole 33, and may be any penetration portion through which the needle tube 4 can penetrate for engagement therewith, for example a hook-like portion whose circumference is partially fractured.

As the protector 2A is moved relative to the needle tube 4 in a direction of the tip end from the above use state (the first attitude) and when the needle tip 41 passes the third hole 33 of the third area 23, the engagement between the needle tube 4 and the third hole 33 is released. As a result, due to the urging force applied by the above-mentioned urging means, the protector 2A is elastically displaced (deformed) into the attitude shown in FIG. 2 (hereinafter, this attitude is referred to as the "second attitude").

That is, in the second attitude, as compared with the state of the first attitude, the protector 2A is displaced (deformed) in such a way that the first area 21 pivots counterclockwise as seen in FIG. 1 relative to the rear connection portion 24

(needle tube 4). As a result, the first-area inclination angle becomes smaller than that in the first attitude, which angle is obtained as θ' where θ'<θ.

Following this, the third area 23, the front connection portion 25, and the cover portion 26 are also displaced (pivoted) relative to the rear connection portion 24 (needle tube 4), so that the distal end of the needle tip 41 of the needle tube 4 is covered with the cover portion 26. The state in which the protector 2A thus covers the needle tip 41 of the needle tube 4, namely the state shown in FIG. 2, is hereinafter referred to as the "needle-tip accommodating state".

In the second attitude (needle-tip accommodating state) described above, the first area 21 of the protector 2A functions as a brake acting on the needle tube 4, thereby prohibiting (inhibiting) relative movement of the protector 2A along the longitudinal direction of the needle tube 4. That is, since the first-area inclination angle becomes smaller than that in the first attitude due to the urging force of the above-mentioned urging means, the inner surface of the first hole 31 comes into pressure contact with the outer peripheral surface of the needle tube 4, thus generating or increasing a frictional force between the inner surface of the first hole 31 and the outer peripheral surface of the needle tube 4. This frictional force acts as a braking force with respect to the protector 2A, thereby prohibiting (inhibiting) the movement of the protector 2A along the longitudinal direction of the needle tube 4.

Due to the above arrangement, in the puncturing instrument 1A, the needle tip 41 of the needle tube 4 does not project through the protector 2A once the needle-tip accommodating state is attained. As a result, it is possible to prevent accidental needle sticks from occurring during needle disposal or the like, thereby ensuring a high level of safety.

Further, since the longitudinal movement of the protector 2A relative to the needle tube 4 is prohibited due to the braking action of the first area 21, there is no need to provide a special structure for locking the protector 2A to the needle tube 4 (for example, locally increasing the outer diameter, providing a convex portion in the outer peripheral portion, binding the hub 5 and the protector 2A together by strings etc). As a result, the tip end of the needle tube 4 can be formed to have a smooth outer peripheral surface that does not require special machining or the like, thereby avoiding a reduction in strength or an increase in insertion resistance. Also, for the same reason mentioned above, the protector 2A can be used in combination with existing needle bodies and therefore has great generality in its application.

Further, the protector 2A according to this embodiment has means for applying such a force to the first area 21 (the plate-like portion near the first hole 31) as to make the first-area inclination angle θ' become smaller when the tip end portion of the protector 2A is pressed in the base end direction in the second attitude.

That is, when a pressing force such as indicated by the arrow A in FIG. 2 is applied to the protector 2A, the pressing force A is transmitted via the third area 23 and the front connection portion 25 to reach the first area 21, where it acts to make the first-area inclination angle θ' become smaller. As a result, the frictional force (braking force acting on the protector 2A) between the inner surface of the first hole 31 and the outer peripheral surface of the needle tube 4 is further increased to resist the pressing force A, thereby prohibiting (inhibiting) the movement of the protector 2A more reliably. Therefore, even in the case where the pressing force A is applied, it is possible to more reliably prevent the needle tip 41 from projecting through the protector 2A, thus ensuring a particularly high level of safety.

Note that, even in the event that the protector 2A slightly moves in a base end direction upon application of a particularly strong pressing force A, the needle tip 41 abuts with the inner surface of the cover portion 26 so that the needle tip 41 does not project through the protector 2A.

Likewise, when a pressing force such as indicated by the arrow B in FIG. 2 is applied to the protector 2A, the pressing force acts to make the first-area inclination angle θ' become smaller. Therefore, even in the case where the pressing force B is applied, it is possible to more reliably prevent the protector 2A from dislodging (falling off) from the needle tip 41, thus ensuring a particularly high level of safety.

The first-area inclination angle θ in the first attitude is not particularly limited; however, it is preferably not less than 60 degrees, and is more preferably substantially a right angle as in this embodiment. Further, although its preferred size depends on the outer diameter d of the needle tube 4, in general, the inner diameter D of the first hole 31 is preferably about 0.01 to 1 mm, and more preferably about 0.05 to 0.2 mm, larger than the outer diameter d of the needle tube 4.

If the first-area inclination angle θ or the inner diameter D of the first hole 31 in the first attitude is within the above-described range, the frictional force between the inner surface of the first hole 31 and the outer peripheral surface of the needle tube 4 (the braking force acting on the protector 2A) becomes large in the second attitude, thereby more reliably prohibiting (inhibiting) the relative movement of the protector 2A along the longitudinal direction of the needle tube 4.

Note that, according to the present invention, the first hole 31 may be one whose circumference is partially fractured (i.e. may be C-shaped or the like)(the same applies to the second hole 32).

Further, while the shape of the second hole 32 or the third hole 33 is not limited to a round shape as far as it allows sliding movement with the needle tube 4, in the case where it is a round shape, the inner diameter thereof is preferably about 0.05 to 1 mm larger than the inner diameter D of the first hole 31 from the viewpoint of reducing the sliding resistance in the first attitude.

In general, the thickness of the plate-like member (first area 21) that forms the protector 2A is preferably on the order of 0.05 to 2 mm, and more preferably on the order of 0.06 to 0.2 mm, although its preferred value varies according to the constituent material of the plate-like member, the outer diameter of the needle tube 4, and the like. Within the above-described range, when a relatively large thickness is set, the braking force that acts on the protector 2A in the second attitude and the protection property of the needle tip 41 become particularly excellent, whereas when a relatively small thickness is set, the workability and the ease of sliding movement with respect to the needle tube 4 in the first attitude become particularly excellent.

The constituent material for the plate-like member which forms the protector 2A is not particularly limited and examples thereof may include, various types of metallic materials such as stainless steel, aluminum or aluminum alloy, iron, nickel alloy, titanium or titanium alloy, and copper or copper type alloy, polyolefins such as polyethylene, polypropylene, polybutadiene, and an ethylene/vinyl acetate copolymer, polyvinyl chloride, polyurethane, polystyrene, polymethyl methacrylate, polycarbonate, polyamide, polyesters such as polyethylene terephthalate, and polybutylene terephthalate, and various types of resin materials such as acrylic resins, ABS resin, AS resin, ionomer, polyacetal, polyphenylene sulfide, and polyetheretherketone. Of those, preferred are the various types of metallic materials. Further, a combination of two or more of the above mentioned materials may be used.

Next, an example method of using the puncturing instrument 1A will be described based on FIGS. 1 and 2.

First, the puncturing instrument 1A is set in the use state (the state shown in FIG. 1) and the tip end portion of a syringe (not shown) is inserted into the base end portion of the hub 5, thereby fitting the puncturing instrument 1A to the syringe. In this state, the needle tube 4 is punctured into a blood vessel of the patient (living body), and a plunger equipped to the syringe is operated to carry out blood collection or infusion of medical solutions with respect to the patient.

Then, upon completing the collection of blood or the infusion of medical solutions, the needle tube 4 is withdrawn from the blood vessel of the patient.

Thereafter, the hub 5 is fixedly grasped by one hand, and using the other hand or tweezers etc, the protector 2A is moved relative to the needle tube 4 in a tip end direction.

In this case, in conventional puncture operations, since a cap is covered over the needle tube 4 after the needle tip 41 is withdrawn from a living body, and the needle tube 4 is inserted from its needle tip 41 into an opening at one end of the cap, if the needle tip 41 misses the opening, this may cause accidental sticking of the needle tip 41 of the needle tube 4 into the fingers pinching the cap. However, according to the present invention, the protector 2A moves in a direction of the tip end of the needle tube 4, thereby effectively preventing the accidental needle sticks described above.

Due to the movement of the protector 2A in the tip end direction, the engagement between the needle tube 4 and the third hole 33 is released when the needle tip 41 of the needle tube 4 passes the third hole 33, so that the protector 2A is deformed elastically (due to its own elasticity) into the second attitude shown in FIG. 2.

When the protector 2A is brought into the second attitude, due to the braking action of the first area 21, the movement of the protector 2A along the longitudinal direction of the needle tube 4 is prohibited (inhibited), so that the protector 2A is stopped in position (stationary) with respect to the needle tube 4 before the needle tip 41 passes the first hole 31. As a result, 1A is brought into the needle-tip accommodating state shown in FIG. 2.

Once the needle tip 41 of the needle tube 4 is accommodated into the protector 2A, the syringe fitted to the hub 5 is removed, thus separating the puncturing instrument 1A and the syringe from each other. Then, the puncturing instrument 1A and the syringe are separately disposed of. As described above, in the puncturing instrument 1A, the needle tip 41 is accommodated in the protector 2A during the needle-tip accommodating state, so that the needle tip 41 does not project through the protector 2A or the protector 2A is not dislodged from needle tip 41. As a result, it is possible to prevent accidental needle sticking of the needle tip 41 into a hand, a finger, or the like during needle disposal or the like, thus ensuring a high level of safety.

Second Embodiment of Protector

Figure 3:
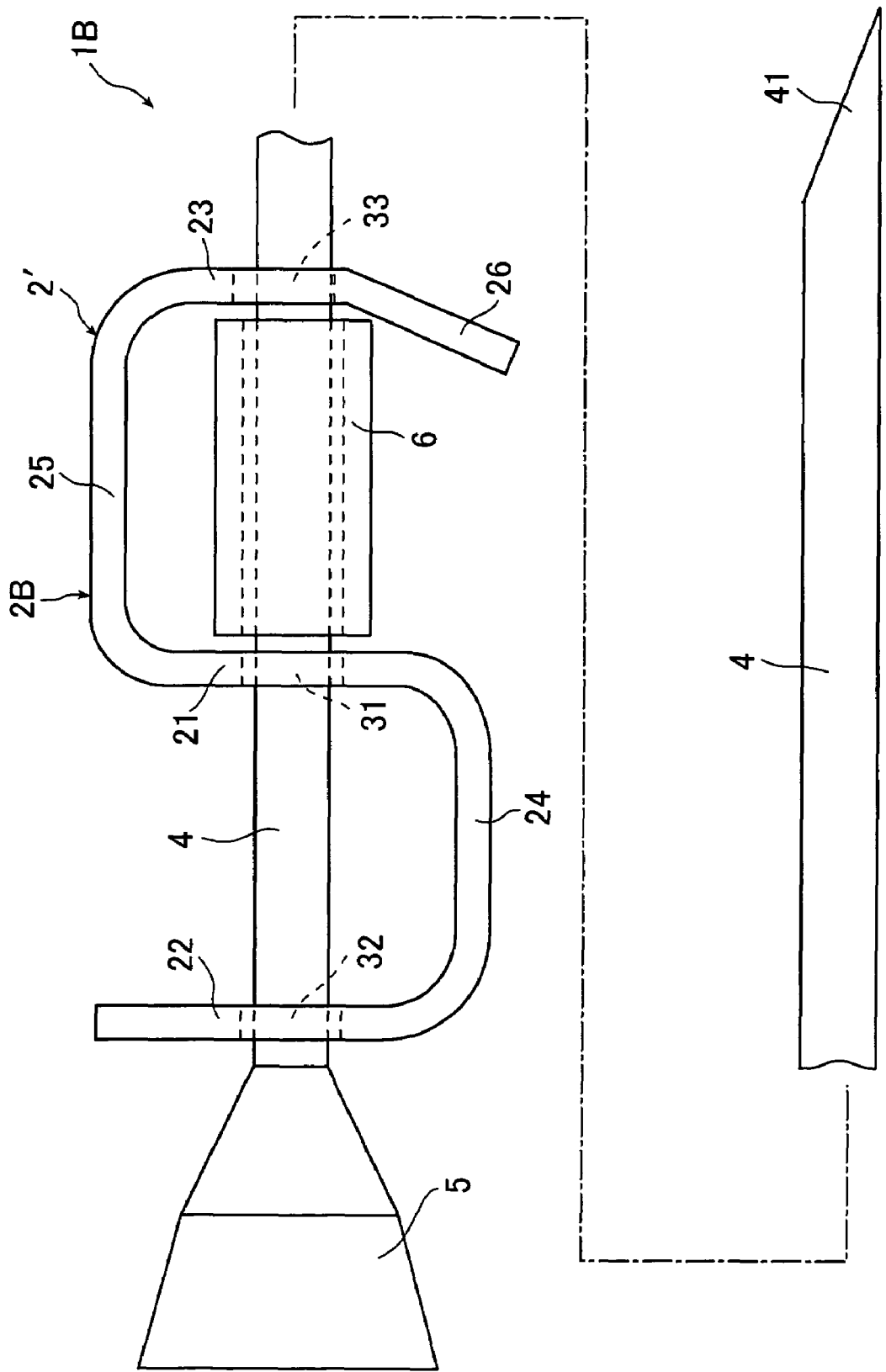
FIG. 3 is a side view (use state) showing a puncturing instrument (injection needle) having a protector according to a second embodiment of the present invention.
Figure 4:
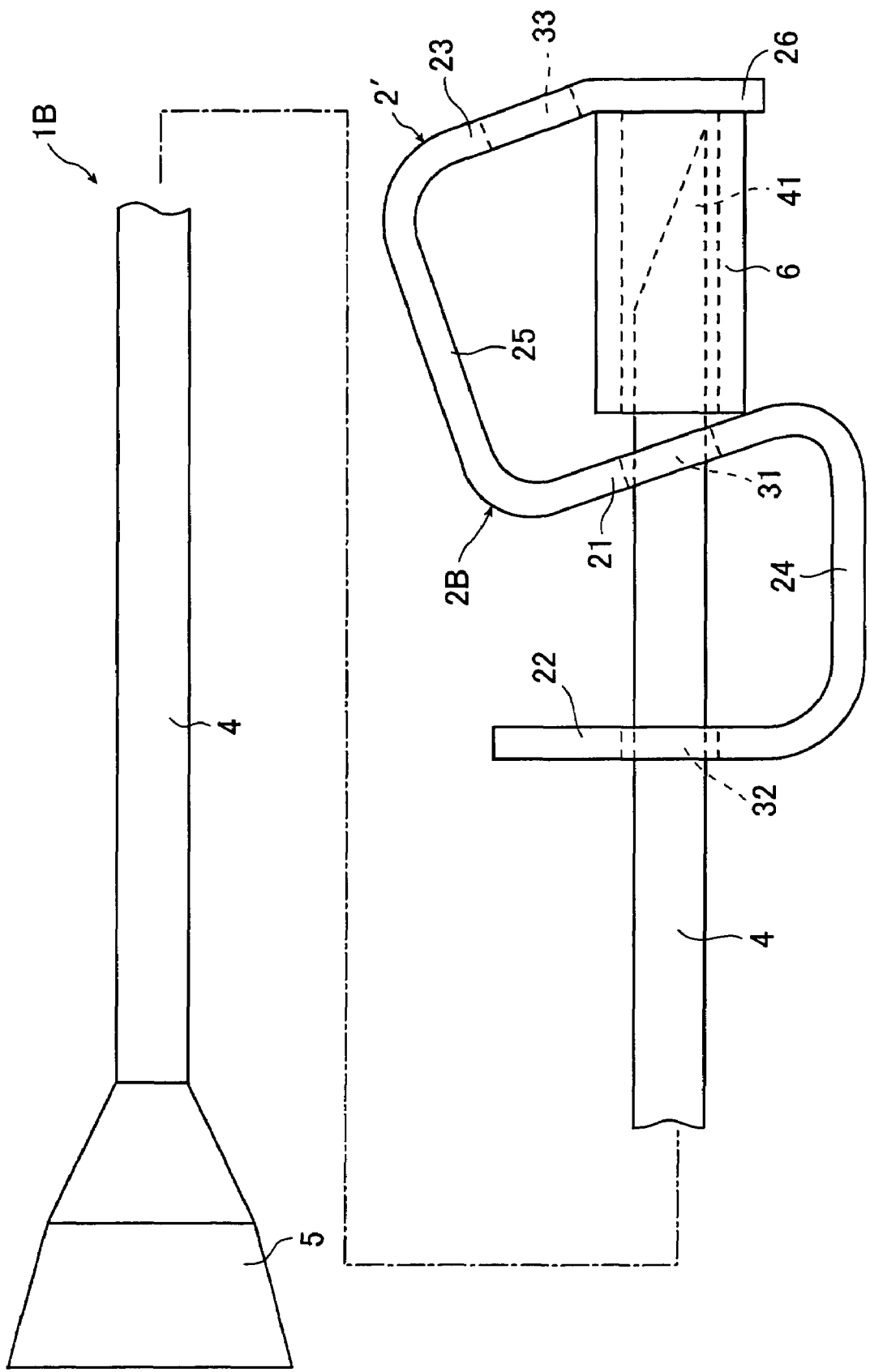
FIG. 4 is a side view (needle-tip accommodating state) showing the puncturing instrument (injection needle) having the protector according to the second embodiment of the present invention.

FIGS. 3 and 4 are each a side view showing a puncturing instrument (injection needle) having a protector according to a second embodiment of the present invention. Note that, in the following description, the needle tip side as seen in FIGS. 3 and 4 is referred to as a "tip end" whereas the hub side is referred to as a "base end", and with the tip end being pointed up, the left-hand side is referred to as "one end" whereas the right-hand side is referred to as "the other end".

Hereinbelow, the second embodiment of the protector of the present invention will be described with reference to those figures. The description will be focused on differences from the aforementioned embodiment, and description of matters identical to those of the aforementioned embodiment will be omitted.

A protector 2B of this embodiment is the same as the protector 2A of the first embodiment described above except that it has a tubular member 6 that serves as a lateral displacement preventing member for preventing lateral displacement of the needle tip 41 of the needle tube 4 in the second attitude. That is, the protector 2B of this embodiment is composed of a protector main body (main body portion) 2' that is the same as the protector 2A of the above-described first embodiment, and the tubular member 6.

Further, a puncturing instrument 1B of this embodiment is composed of the above-described protector 2B, and the needle tube 4 and the hub 5 that are the same as those of the above-described first embodiment.

The tubular member 6 serving as the lateral displacement preventing member mentioned above has a cylindrical shape having a hollow portion through which the needle tube 4 can be penetrated (inserted), and is located between the third hole 33 that is formed in the third area 23 of the protector main body 2' and the first hole 31 that is formed in the first area 21 thereof.

That is, in the first attitude (use state) shown in FIG. 3, the needle tube 4 penetrates through the second hole 32, the first hole 31, the hollow portion of the tubular member 6, and the third hole 33 of the protector 2B in the stated order.

Then, in the second attitude (needle-tip accommodating state) shown in FIG. 4, the needle tip 41 is located inside the tubular member 6 to be covered by the tubular member 6.

Further, the opening at the tip end of the tubular member 6 is covered and sealed by the cover portion 26 of the protector main body 2'. That is, the tubular member 6 also functions as a cap member for covering the needle tip 41 in the second attitude.

Due to the above-described construction, in addition to providing the same effects as those of the protector 2A of the first embodiment described above, the protector 2B of this embodiment also serves to prevent the needle tip 41 from being displaced in a lateral direction (a direction perpendicular to the longitudinal direction) in the second attitude. As a result, in the needle-tip accommodating state, even in the event that a strong external force is exerted on the protector 2B in the lateral direction, for example, the projection of the needle tip 41 can be prevented more reliably, thereby enhancing safety.

Further, the entirety of the needle tip 41 is covered by the tubular member 6 and the cover portion 26 so that it is possible to prevent (restrain) blood (body fluid) remaining around or in the interior of the needle tip 41 from dripping, thereby effectively preventing contamination by the blood (body fluid).

The constituent material for the tubular member 6 is not particularly limited, and examples thereof may include: various types of metallic materials such as stainless steel, aluminum or aluminum alloy, titanium or titanium alloy, iron, nickel alloy, and copper or copper type alloy; polyolefins such as polyethylene, polypropylene, polybutadiene, and an ethylene/vinyl acetate copolymer, polyvinyl chloride, polyurethane, polystyrene, polymethyl methacrylate, polycarbonate, polyamide, polyesters such as polyethylene terephthalate, and polybutylene terephthalate; various types of resin materials such as acrylic resins, ABS resin, AS resin, ionomer, polyacetal, polyphenylene sulfide, and polyetheretherketone; various rubber materials; and various thermoplastic elastomers, while a combination of two or more of those materials may also be used.

If the constituent materials of the tubular member 6 include various rubber materials or various thermoplastic elastomers, in the second attitude, the cover portion 26 can be brought into more intimate contact with the opening at the tip end of the tubular member 6, thereby making it possible to more effectively prevent the dripping of the blood (body fluid) remaining around or in the interior of the needle tip 41.

Third Embodiment of Protector

Figure 5:
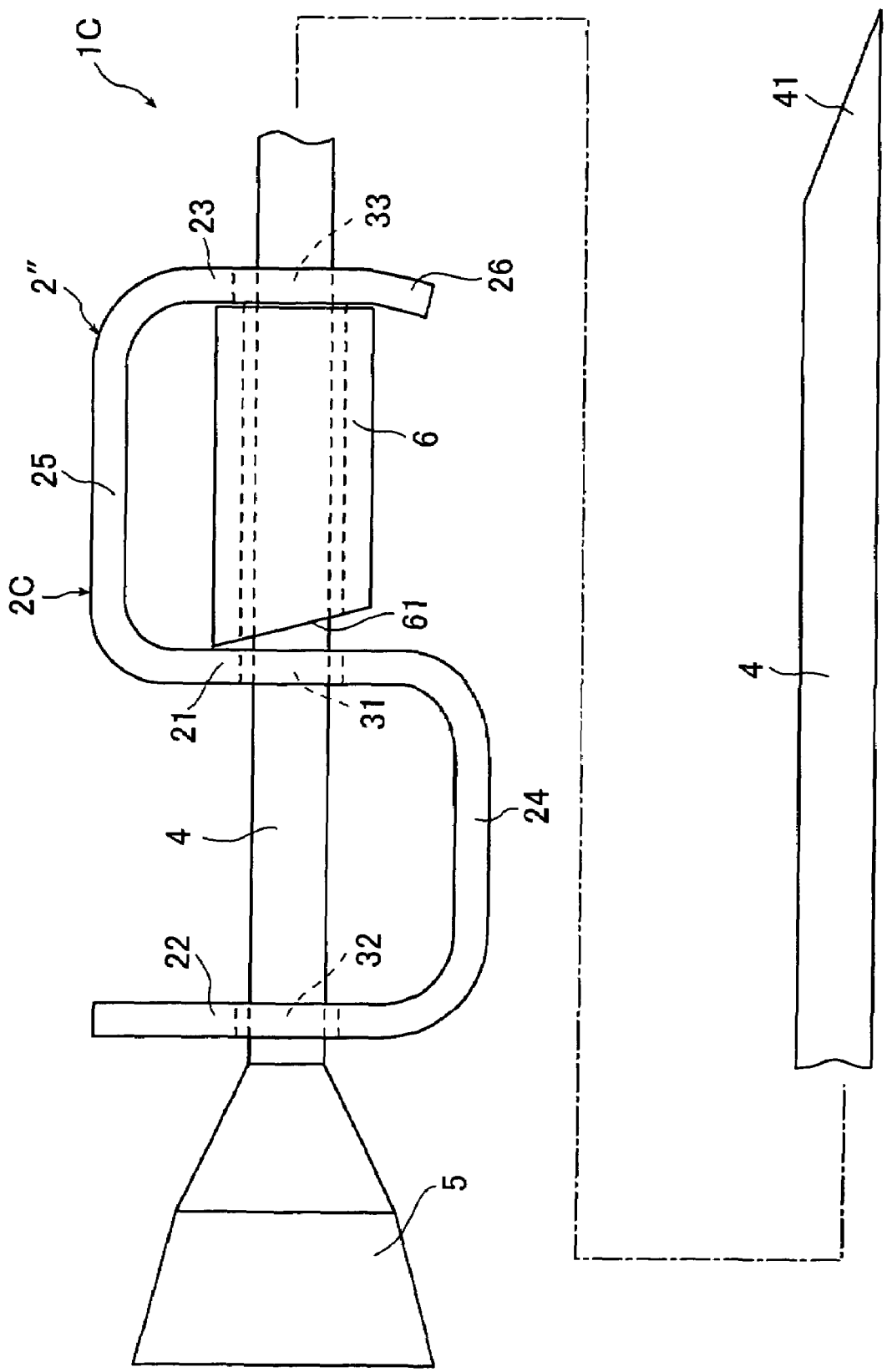
FIG. 5 is a side view (use state) showing a puncturing instrument (injection needle) having a protector according to a third embodiment of the present invention.
Figure 6:
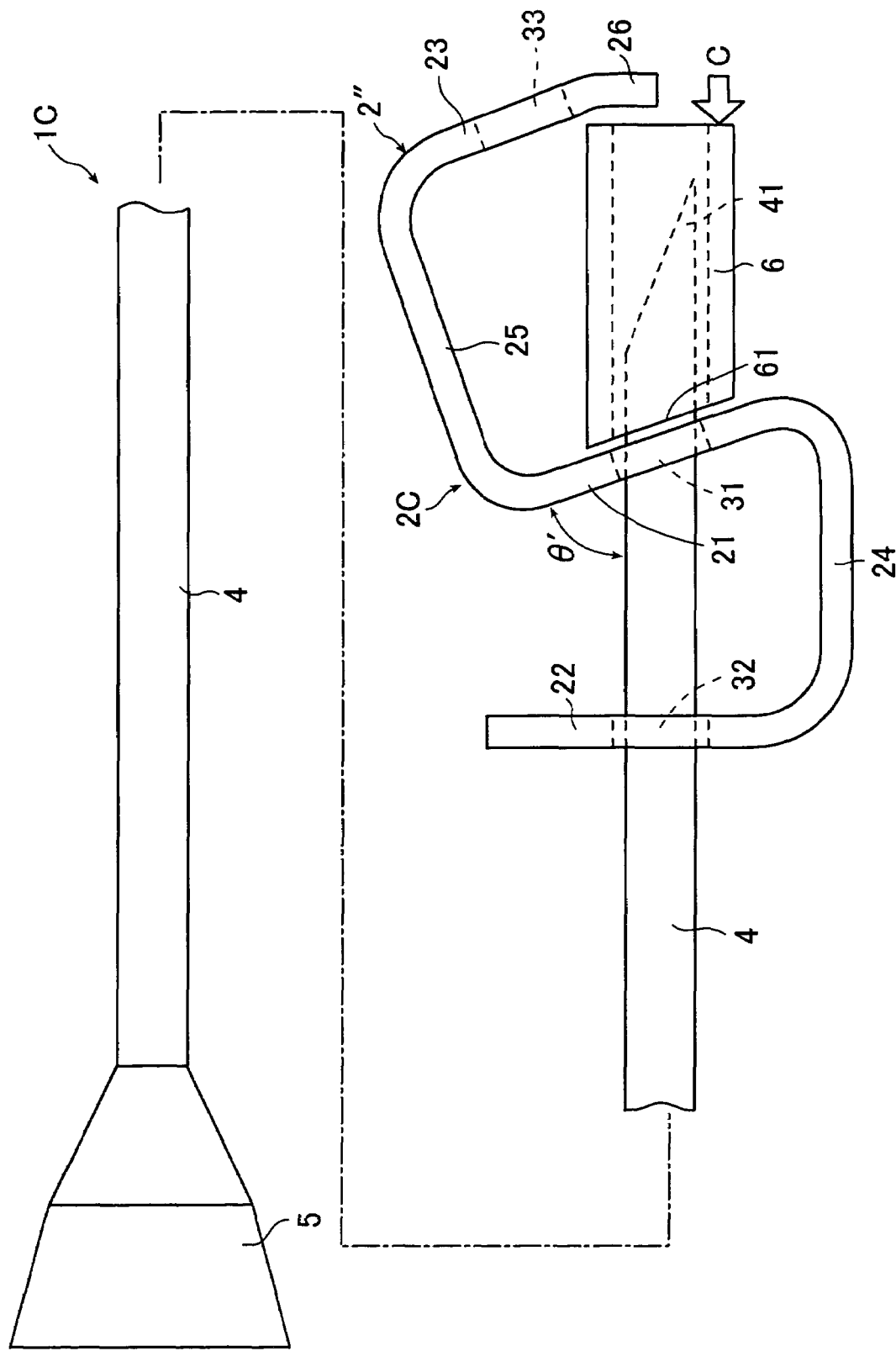
FIG. 6 is a side view (needle-tip accommodating state) showing the puncturing instrument (injection needle) having the protector according to the third embodiment of the present invention.

FIGS. 5 and 6 are each a side view showing a puncturing instrument (injection needle) having a protector according to a third embodiment of the present invention. Note that, in the following description, the needle tip side as seen in FIGS. 5 and 6 is referred to as a "tip end" whereas the hub side is referred to as a "base end", and with the tip end being pointed up, the left-hand side is referred to as "one end" whereas the right-hand side is referred to as "the other end".

Hereinbelow, the third embodiment of the protector of the present invention will be described with reference to those figures. The description will be focused on differences from the aforementioned embodiments, and description of matters identical to those of the aforementioned embodiments will be omitted.

A protector 2C of this embodiment is the same as the protector 2B of the second embodiment described above except that the shape of the tubular member serving as the above-described lateral displacement preventing member is different. That is, the protector 2C of this embodiment is composed of a protector main body (main body portion) 2″ that is the same as the protector 2B of the above-described first embodiment, and the tubular member 6.

Further, a puncturing instrument 1C of this embodiment is composed of the above-described protector 2C, and the needle tube 4 and the hub 5 that are the same as those of the first embodiment described above.

The tubular member 6 serving as the above-described lateral displacement preventing member has a cylindrical shape having a hollow portion through which the needle tube 4 can be penetrated (inserted), and is located between the third hole 33 that is formed in the third area 23 of the protector main body 2′ and the first hole 31 that is formed in the first area 21 thereof.

That is, in the first attitude (use state) shown in FIG. 5, the needle tube 4 penetrates through the second hole 32, the first hole 31, the hollow portion of the tubular member 6, and the third hole 33 of the protector 2 in the stated order.

The base end face of the tubular member 6 is formed as an inclined surface 61 that is inclined relative to the plane perpendicular to the needle tube 4. The inclination direction of the inclined surface 61 is the same as the inclination direction of the first area 21 in the second attitude (needle-tip accommodating state) shown in FIG. 6.

Note that, although omitted in the drawing, rotation preventing means for preventing the tubular member 6 from rotating with respect to the protector main body 2″ is provided to the protector 2C.

Due to the above-described construction, in addition to providing the same effects as those of the protector 2A of the first embodiment described above, the protector 2C of this embodiment also serves to prevent the needle tip 41 from being displaced in a lateral direction (a direction perpendicular to the longitudinal direction) in the second attitude, in the same manner as the protector 2B of the second embodiment described above.

Further, according to this embodiment, there is provided means (the inclined surface 61) for exerting such a force on the first area 21 (the plate-like member near the first hole 31) as to make the first-area inclination angle θ′ become smaller when such a pressing force as indicated by the arrow C in FIG. 6 is exerted on the protector 2C in the second attitude, that is, when the tip end portion of the tubular member 6 is pressed in the base end direction.

That is, the above-mentioned pressing force C is transmitted by way of the inclined surface 61 of the tubular member 6 to reach the first area 21, where it acts to make the first-area inclination angle θ′ become smaller. As a result, the frictional force (braking force acting on the protector 2C) between the inner surface of the first hole 31 and the outer peripheral surface of the needle tube 4 is further increased to resist the pressing force C, thereby prohibiting (inhibiting) the movement of the protector 2C more reliably. Therefore, even in the case where the pressing force C is applied, it is possible to more reliably prevent the needle tip 41 from projecting through the protector 2, thus ensuring a particularly high level of safety.

Note that, as in the second embodiment described above, an arrangement may be employed in this embodiment as well in which the cover portion 26 seals the opening at the tip end of the tubular member 6 in the second attitude.

Fourth Embodiment of Protector

Figure 7:
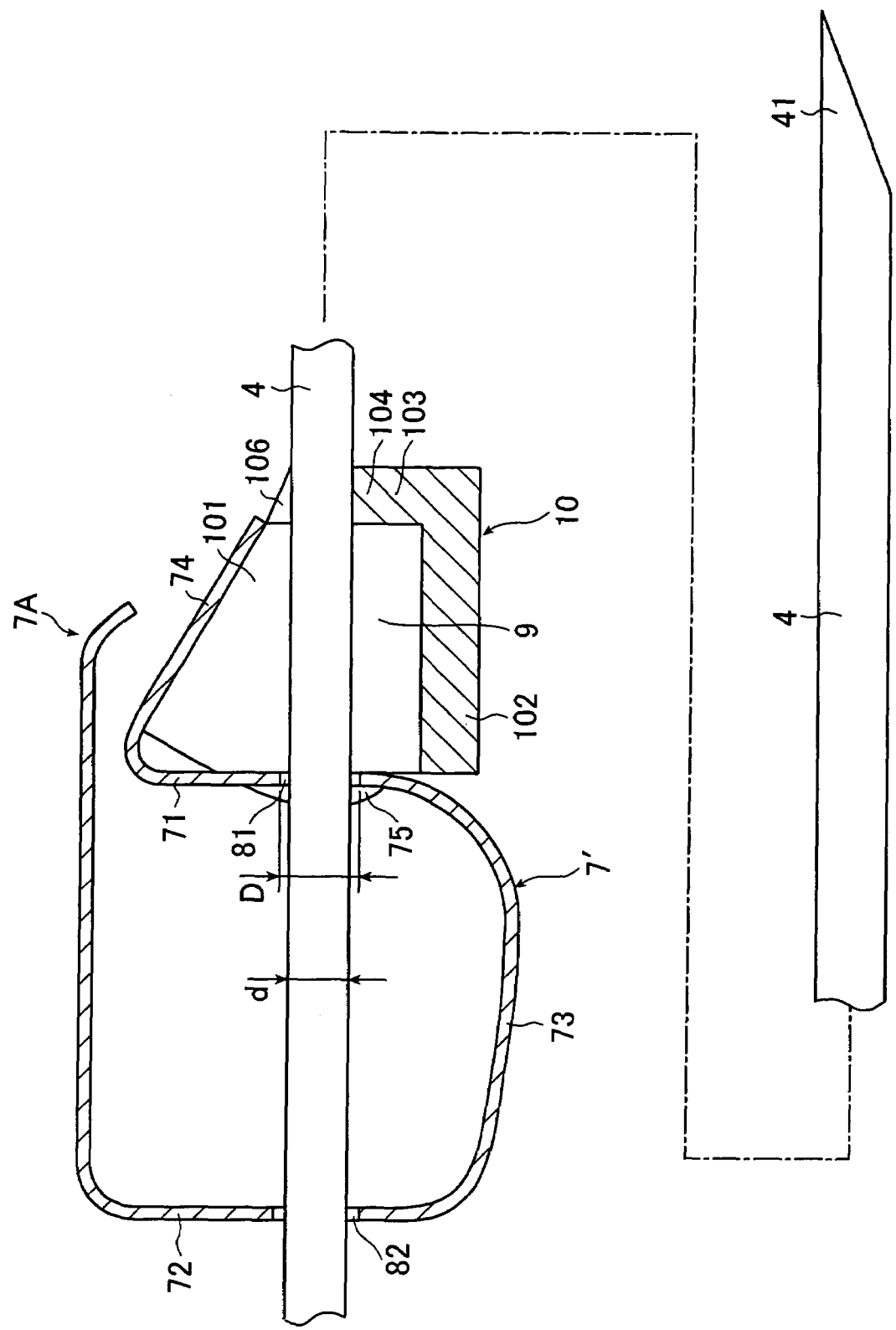
FIG. 7 is a cross-sectional side view showing a state where a protector according to a fourth embodiment of the present invention is fitted to a needle body, in which the protector is shown as being in a first attitude.
Figure 8:
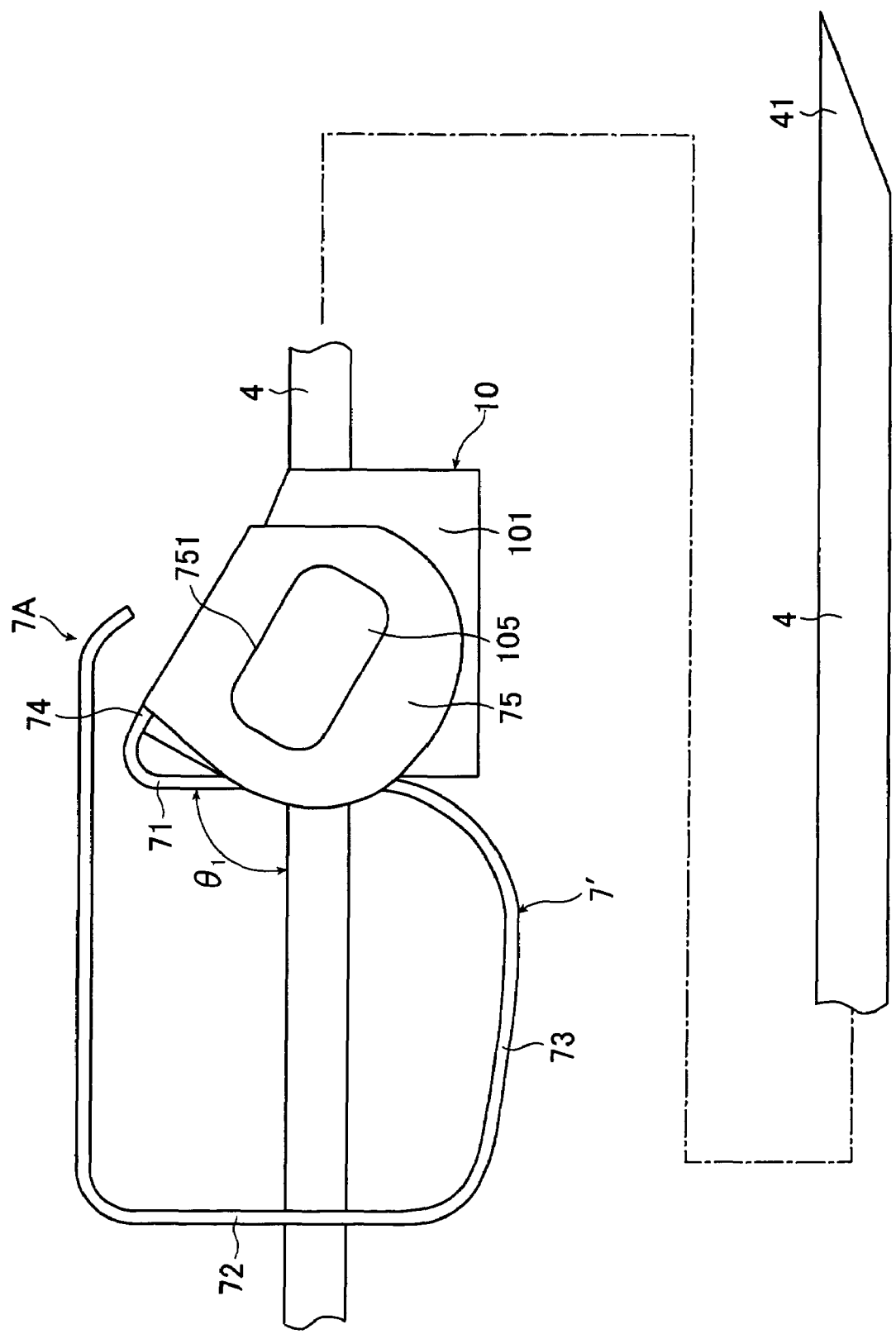
FIG. 8 is a side view showing a state where the protector according to the fourth embodiment of the present invention is fitted to the needle body, in which the protector is shown as being in the first attitude.
Figure 9:
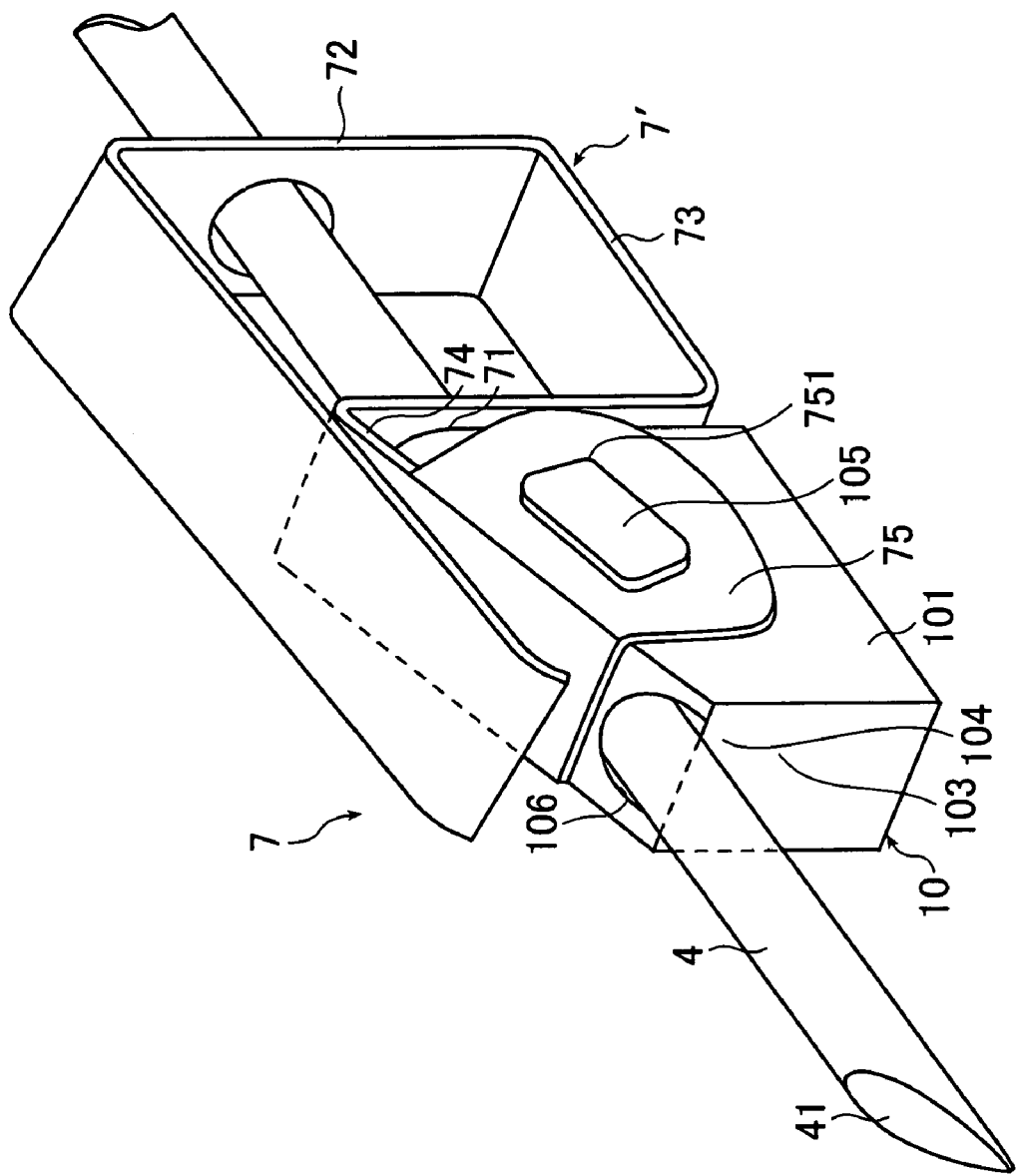
FIG. 9 is a perspective view showing a state where the protector according to the fourth embodiment of the present invention is fitted to the needle body, in which the protector is shown as being in the first attitude.
Figure 10:
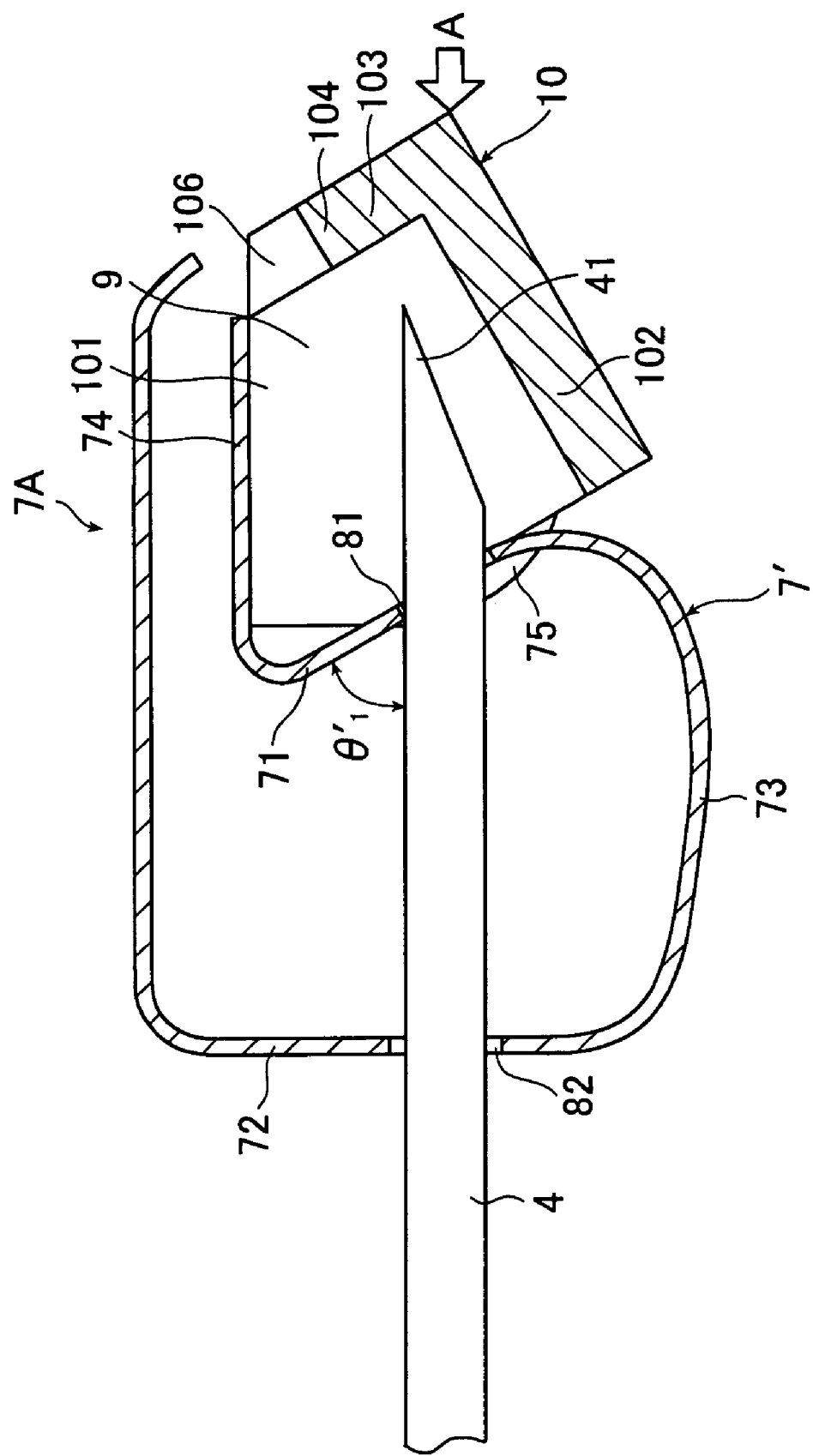
FIG. 10 is a cross-sectional side view in which the protector shown in FIG. 7 is shown as being in a second attitude.

FIGS. 7 and 10 are each a cross-sectional side view showing a protector according to a fourth embodiment of the present invention. FIG. 8 and FIG. 9 are a side view and a perspective view of the protector shown in FIG. 7, respectively. Note that, in the following description, the needle tip side as seen in FIGS. 7, 8, and 10 is referred to as a "tip end" whereas the hub side is referred to as a "base end", and with the tip end being pointed up, the left-hand side is referred to as "one end" whereas the right-hand side is referred to as "the other end".

Referring to those figures, a protector 7A constitutes a part of a puncturing instrument by being fitted to the needle tube (needle body) 4 which has the sharp needle tip 41 at its tip end and whose base end is fixed to a hub (not shown).

In FIGS. 7 through 9, the protector 7A of this embodiment is shown as being in an attitude equivalent to the first attitude of the protector according to each of the first through third embodiments described above, that is, in an attitude in which the protector 7A is capable of relative movement along the longitudinal direction (axial direction) of the needle tube 4 (this attitude will be referred to as the "first attitude" in the description of subsequent embodiments including this embodiment).

On the other hand, in FIG. 10, the protector 7A of this embodiment is shown as being in an attitude equivalent to the second attitude of the protector according to each of the first through third embodiments described above, that is, in an attitude in which the needle tip 41 of the needle tube 4 is covered so that the relative movement of the protector 7A along the longitudinal direction of the needle tube 4 is prohibited (this attitude will be referred to as the "second attitude" in the description of subsequent embodiments including this embodiment).

The protector 7A of this embodiment has a protector main body 7′ formed by deforming (bending) a plate-like member constructed of a metallic material, and a plastic member 10 fixed (secured) to the protector main body 7'.

As shown in FIG. 7, the protector main body 7' has a first area (brake portion) 71 in which a first hole (hole) 81 is formed, a second area 72 which is provided on the base end side (needle root side) of the first area 71 and in which a second hole 82 is formed, and a third area 73 connecting the other end of the first area 71 and the other end of the second area 72 with each other.

That is, as seen in side view (FIG. 7), the first area 71, the second area 72, and the third area 73 are formed to have a substantially C shape as a whole.

The needle tube 4 is penetrated through the first hole 81 and the second hole 82. The first hole 81 is preferably round in shape.

Further, the protector main body 7' has a fourth area 74 provided so as to extend from one end portion of the first area 71 in the tip end direction, and fifth areas 75, 75 provided so as to extend substantially parallel to each other from both side portions of the fourth area 74 in the direction toward the other end.

That is, in contrast to the side view of FIG. 7, in front view as seen from the needle tip side, the fourth area 74 and the fifth areas 75, 75 are formed to have a substantially C shape as a whole, and both the fifth areas 75, 75 are located so as to sandwich the needle tube 4 from both sides. The positional relationship among those areas are explicitly shown in FIG. 9.

As shown in FIGS. 8 and 9, a substantially rectangular (elliptical), elongate hole 751 is formed in each of the fifth areas 75, 75.

Further, as shown in FIGS. 7 through 9, according to this embodiment, the fourth area 74 is inclined such that, in the first attitude, the fourth area 74 comes progressively closer to the needle tube 4 as it extends in the tip end direction. Due to this arrangement, as shown in FIG. 10, the fourth area 74 does not overhang to the outside upon displacement (deformation) into the second attitude, which contributes to the miniaturization of the protector 7A as a whole.

The protector main body 7' described above is constructed of a metallic material. As a result, the frictional force between the inner surface of the first hole 81 and the surface of the needle tube 4 becomes sufficiently large in the second attitude, thus allowing the braking action of the first area 71 (brake portion) to be exerted with reliability. Although the metallic material constituting the protector main body 7' is not particularly limited, various kinds of metallic materials such as stainless steel, aluminum or aluminum alloy, iron, nickel alloy, titan or titan alloy, and copper or copper-based alloy may be given.

Note that, while in this embodiment the respective portions of the protector main body 7' are formed integrally with each other, according to the present invention, the protector main body 7' may be also composed of two or more parts.

The plastic member 10 is installed between both the fifth areas 75, 75 of the protector main body 7'. As shown in FIG. 7, the plastic member 10 has side wall portions 101, 101 respectively arranged inside the fifth areas 75, 75, and a connecting wall 102 connecting the respective other end portions of both the side wall portions 101, 101 with each other.

The side wall portions 101, 101 are respectively provided substantially parallel to the fifth areas 75, 75. That is, as seen from the front, the side wall portions 101, 101 and the connecting wall 102 are formed to have a substantially C shape as a whole.

Due to the above arrangement, the protector 7A of this embodiment has a needle-tip accommodating space 9 formed by being surrounded by the side wall portions 101, 101 and the connecting wall 102. As shown in FIG. 10, the needle tip 41 of the needle tube 4 is accommodated in the needle-tip accommodating space 9 in the second attitude.

Further, when accommodated into a needle-tip accommodating space 9 in the second attitude, the needle tip 41 is covered substantially from all around by the first area 71, the fourth area 74, the side wall portions 101, 101, and the connecting wall 102. As a result, it is possible to prevent blood or the like remaining on the surface or in the interior of the needle tip 41 from adhering to an operator or a surrounding object, thereby preventing contamination.

Projecting portions 105, 105 that project to the exterior are respectively formed in the side wall portions 101, 101. As shown in FIGS. 8 and 9, the projecting portion 105 has a shape corresponding to that of the elongate hole 751 of the fifth area 75. Each of the projecting portions 105, 105 is inserted (fitted) into each of the elongate holes 751, 751. As a result, the plastic member 10 is fixed (secured) to the protector main body 7'. Note that, needless to say, the method for fixing the plastic member 10 and the protector main body 7' to each other is not limited to the above, and any method may be employed such as adhesion using an adhesive.

The plastic member 10 further has a tip end wall 103 that covers the needle-tip accommodating space 9 from the tip end side. As shown in FIGS. 9 and 10, a notch portion 106 is formed in an upper side of the tip end wall 103 as seen in FIG. 7. In the first attitude, the needle tube 4 passes through the notch portion 106 to project from the protector 7A in the tip end direction.

The edge portion of the notch portion 106 serves as a needle-body abutting portion 104 that abuts with the needle tube 4 in the first attitude. The needle-body abutting portion 104 is preferably formed as a curved surface of an arcuate shape that conforms with the needle body surface.

In the first attitude, the needle-body abutting portion 104 abuts with the needle tube 4. That is, as will be described later, the plastic member 10 is urged in such a direction as to pivot counterclockwise as seen in FIG. 7 due to the elasticity (spring property) between a part of the first area 71 and a part of the third area 73 of the protector main body 7', and this urging force allows the needle-body abutting portion 104 to be brought into pressure contact with the needle tube 4 in the first attitude.

Note that, the construction of the plastic member 10 is not limited to the one shown in the drawing. For example, the plastic member 10 may have a tubular shape having the needle-body abutting portion as a hole.

The plastic member 10 including the needle-body abutting portion 104 as described above is constructed of a resin material (synthetic resin material). Thus, in the first attitude, the frictional resistance between the needle-body abutting portion 104 and the surface of the needle tube 4 is alleviated, thereby reducing the sliding resistance of the protector 7A with respect to the needle tube 4. As a result, in the first attitude, the protector 7A can be moved smoothly (with a relatively small operational force) along the longitudinal direction (axial direction) of the needle tube 4.

The resin material constituting the plastic member 10 (needle-body abutting portion 104) is not particularly limited, and examples thereof may include various types of resins such as polyethylene, polypropylene, polyurethane, polystyrene, polycarbonate, polyester, ABS resin, AS resin, fluorine-based resins, and polyacetal.

Note that, in the present invention, it is sufficient that preferably at least the needle-body abutting portion 104 be constructed of a resin material. Further, the surface of the needle-body abutting portion 104 may be also constructed of (coated by) a material having a particularly small coefficient of friction (frictional resistance), for example, the fluorine-based resin mentioned above.

Note that, the contact surface of the needle-body abutting portion 104 with the needle tube 4 may be, for example, flat, V-shaped, C-shaped, or the like.

During use of the puncturing instrument (when it is punctured into a living body or the like), the protector 7A described above is located on the needle root side of the needle tube 4 in the first attitude shown in FIGS. 7 through 9.

In this first attitude, the needle tube 4 penetrates through the second hole 82 and the first hole 81 and further passes through the needle-body accommodating space 9 and the notch portion 106 to project through the tip end of the protector 7A.

Further, in the first attitude, the first area 71 and the second area 72 are both positioned substantially perpendicular to the needle tube 4.

The protector 7A is capable of being displaced (deformed) from the above first attitude into the second attitude shown in FIG. 10 for covering the needle tip 41. In this second attitude, the angle formed between the first area 71 and the third area 73 in the protector main body 7' is smaller than that in the first attitude. That is, the protector 7A is displaced (deformed) from the first attitude to the second attitude by being deformed in such a way that the first area 71 and the third area 73 are narrowed close (the first area 71 comes closer to the third area 73).

Such displacement (deformation) from the first attitude into the second attitude is caused by the elasticity (elastic force) between a part of the first area 71 and a part of the third area 73 in the protector main body 7'.

That is, in a natural state (the state in which the protector 7A is not fitted to the needle tube 4) in which no external force is imparted to the protector 7A, the angle formed between the first area 71 and the third area 73 is even smaller than that in the state shown in FIG. 10. The protector 7A is subjected to deformation (elastic deformation) from the above natural state in such a way that the first area 71 and the third area 73 are spread open (the first area 71 moves away from the third area 73) before being fitted to the needle tube 4.

Due to the above arrangement, in the state where the protector 7A is being fitted to the needle tube 4, the first area 71 is urged in such a direction for making its inclination angle (the angle indicated by $\theta_1$ in FIG. 8 and $\theta_1'$ in FIG. 10) relative to the needle tube 4 become smaller. That is, a part of the first area 71 and a part of the third area 73 in the protector 7A serve as urging means for urging the first area 71 due to elasticity thereof in such a direction for making the inclination angle $\theta$ of the first area 71 relative to the needle tube 4 become smaller.

As shown in FIG. 7, in the first attitude, the abutment of the needle-body abutting portion 104 with the surface of the needle tube 4 serves to inhibit the protector 7A from being deformed in such a way as to make the first-area inclination angle become smaller due to the urging force of the above-mentioned urging means. As a result, the first-area inclination angle $\theta_1$ in the first attitude is kept at a substantially right angle as described above. In this specification, the "inclination angle of the first area 71 relative to the needle tube 4" is defined in the same manner as the "inclination angle of the first area 21 relative to the needle tube 4" in the first embodiment described above.

Therefore, in the first attitude, a gap is formed between the first hole 81 and the needle tube 4 so that practically no frictional force acts between the inner surface of the first hole 81 and the surface of the needle tube 4, or such a force is relatively small. That is, in the first attitude, the first area 71 does not exert its braking action.

As described above, the needle-body abutting portion 104 has a function of reserving the braking action of the first area 71 by abutting with the needle tube 4 in the first attitude to thereby prevent the first-area inclination angle from becoming smaller (changed).

That is, in the first attitude, the protector 7A is in a braking-action reserving state due to the abutment of the needle-body abutting portion 104 with the needle tube 4.

Thus, while in the first attitude the needle-body abutting portion 104 is in pressure contact with the surface of the needle tube 4 due to the urging force of the above-mentioned urging means, according to the present invention, the needle-body abutting portion 104 is constructed of a resin material as described above so that the protector 7A can be moved smoothly (with a relatively small operational force) relative to the needle tube 4.

As the protector 7A is moved relative to the needle tube 4 in the tip end direction from the first attitude and when the needle-body abutting portion 104 passes the needle tip 41, the needle-body abutting portion 104 is detached (spaced apart) from the needle tube 4. As a result, the protector 7A is released from the braking-action reserving state to be elastically displaced (deformed) into the second attitude due to the urging force of the above-mentioned urging means.

That is, in the second attitude, as compared with the state of the first attitude, the protector 7A is displaced (deformed) in such a way that the first area 71 pivots counterclockwise as seen in FIGS. 7 and 8 relative to the third area 73 (needle tube 4). As a result, as shown in FIG. 10, the first-area inclination angle becomes smaller than that in the first attitude, the angle of which is obtained as $\theta_1'$ where $\theta_1' < \theta_1$.

Following this, the fourth area 74, the fifth area 75, and the plastic member 10 are also displaced (pivoted) relative to the third area 73 (needle tube 4), so that the needle tip 41 is covered by the tip end wall 103 from the tip end side.

In the second attitude described above, the first area 71 of the protector 7A functions as a brake acting with respect to the needle tube 4, thereby prohibiting (inhibiting) the relative movement of the protector 7A along the longitudinal direction of the needle tube 4. That is, since the first-area inclination angle becomes smaller than that in the first attitude due to the urging force of the above-mentioned urging means, the inner surface of the first hole 81 comes into pressure contact with the surface (outer peripheral surface) of the needle tube 4, thus generating or increasing a frictional force between the inner surface of the first hole 81 and the surface (outer peripheral surface) of the needle tube 4. This frictional force acts as a braking force with respect to the protector 7A, thereby prohibiting (inhibiting) the movement of the protector 7A along the longitudinal direction of the needle tube 4.

Due to the above arrangement, the needle tip 41 does not project through the protector 7A once the needle tip 41 is accommodated into the needle-tip accommodating space 9 (once the second attitude is attained).

The first-area inclination angle $\theta_1$ in the first attitude is not particularly limited; however, it is preferably not less than 60 degrees, and is more preferably substantially a right angle as in this embodiment.

Further, although its preferred size depends on the outer diameter d of the needle tube 4, in general, the inner diameter D of the first hole 81 is preferably about 0.01 to 1 mm, and more preferably about 0.05 to 0.2 mm, larger than the outer diameter d of the needle tube 4.

If the first-area inclination angle $\theta_1$ or the inner diameter D of the first hole 81 in the first attitude is within the above-described ranges, the frictional force between the inner surface of the first hole 81 and the surface of the needle tube 4 (the braking force acting on the protector 7A) becomes large in the second attitude, thereby more reliably prohibiting (inhibiting) the relative movement of the protector 7A along the longitudinal direction of the needle tube 4.

Note that, according to the present invention, the first hole 81 may be one whose circumference is partially fractured (i.e. may be C-shaped or the like)(the same applies to the second hole 82).

Further, while the shape of the second hole 82 is not limited to a round shape as far as it allows sliding movement with the needle tube 4, in the case where it is a round shape, the inner diameter thereof is preferably about 0.05 to 1 mm larger than the inner diameter D of the first hole 81 from the viewpoint of reducing the sliding resistance in the first attitude.

Further, the area in the vicinity of the second hole 82 (the contact surface with the needle tube 4) may be constructed of a resin material such as one described above or subjected to bending process so that the contact surface with the needle tube 4 is made smooth. As a result, the frictional force between the inner surface of the second hole 82 and the surface of the needle tube 4 can be reduced. Therefore, a further reduction in the sliding resistance of the protector 7A with respect to the needle tube 4 is attained in the first attitude, with the result that the operation of moving the protector 7A in the tip end direction relative to the needle tube 4 (the operation of covering the needle tip 41 with the protector 7A) can be performed with greater ease and smoothness.

In general, the thickness of the plate-like member (particularly the first area 71) that forms the protector main body 7' is preferably on the order of 0.05 to 2 mm, and more preferably on the order of 0.06 to 0.2 mm, although its preferred value varies according to the constituent material of the plate-like member, the outer diameter of the needle tube 4, and the like. Within the above-described range, when a relatively large thickness is set, the braking force that acts on the protector 7A in the second attitude and the protection property of the needle tip 41 become particularly excellent, whereas when a relatively small thickness is set, the workability and the ease of sliding movement with respect to the needle tube 3 in the first attitude become particularly excellent.

The protector 7A described above has means for applying such a force to the first area 71 (the plate-like member near the first hole 81) as to make the first-area inclination angle $\theta_1'$ become smaller when the tip end portion (the plastic member 10 etc) of the protector 7A is pressed in the base end direction in the second attitude.

That is, for example, when such a pressing force as indicated by the arrow A in FIG. 10 is applied to the tip end portion of the plastic member 10, the pressing force A is transmitted through the fourth area 74 to reach the first area 71, where it acts to make the first-area inclination angle $\theta_1'$ become smaller. As a result, the frictional force (braking force acting on the protector 7A) between the inner surface of the first hole 81 and the surface of the needle tube 4 is further increased to resist the pressing force A, thereby prohibiting (inhibiting) the movement of the protector 7A with greater reliability.

Note that, even in the event that the protector 7A slightly moves in the base end direction upon application of a particularly strong pressing force A, the needle tip 41 abuts with the inner side of the corner (needle-tip receiving portion) formed between the connecting wall 102 and the tip end wall 103, with the result that the needle tip 41 does not project through the protector 7A.

Next, an example method of using the protector 7A will be described in detail.

[1] In a state where the protector 7A that is in the first attitude is located on the base end side of the needle tube 4, the needle tube 4 is punctured into the blood vessel (living body) of a patient or the like to perform blood collection or infusion of medical solutions.

[2] Upon completion of the blood collection or the infusion of the liquid medications, the needle tube 4 is withdrawn from the blood vessel of the patient.

[3] Next, using a hand, tweezers, or the like, the protector 7A is moved in the tip end direction relative to the needle tube 4. As described above, in the present invention, the needle-body abutting portion 104 is constructed of a resin material so that the protector 7A can be moved in the tip end direction relative to the needle tube 4 with a relatively small operational force at this time, thus allowing this operation to be performed smoothly, swiftly, and easily.

[4] When the needle-body abutting portion 104 passes the needle tip 41 to be detached from the needle tube 4 as the protector 7A moves in the tip end direction, the protector 7A is elastically deformed (due to its own elasticity) into the second attitude shown in FIG. 10.

Once the protector 7A is in the second attitude, the movement of the protector 7A along the longitudinal direction of the needle tube 4 is prohibited (inhibited) by the braking action of the first area 71, so that the needle tip 41 is stopped (becomes stationary) with respect to the needle tube 4 before it passes the first hole 81.

[5] After the needle tip 41 of the needle tube 4 is accommodated into the protector 7A (needle-tip accommodating space 9), those are discarded for disposal.

At this time, as described above, the needle tip 41 is accommodated inside the protector 7A so that the needle tip 41 does not project through the protector 7A or the protector 7A is not dislodged from the needle tip 41. As a result, it is possible to prevent accidental sticking of the needle tip 41 into a hand, a finger, etc during needle disposal or the like.

Fifth Embodiment of Protector

Figure 11:
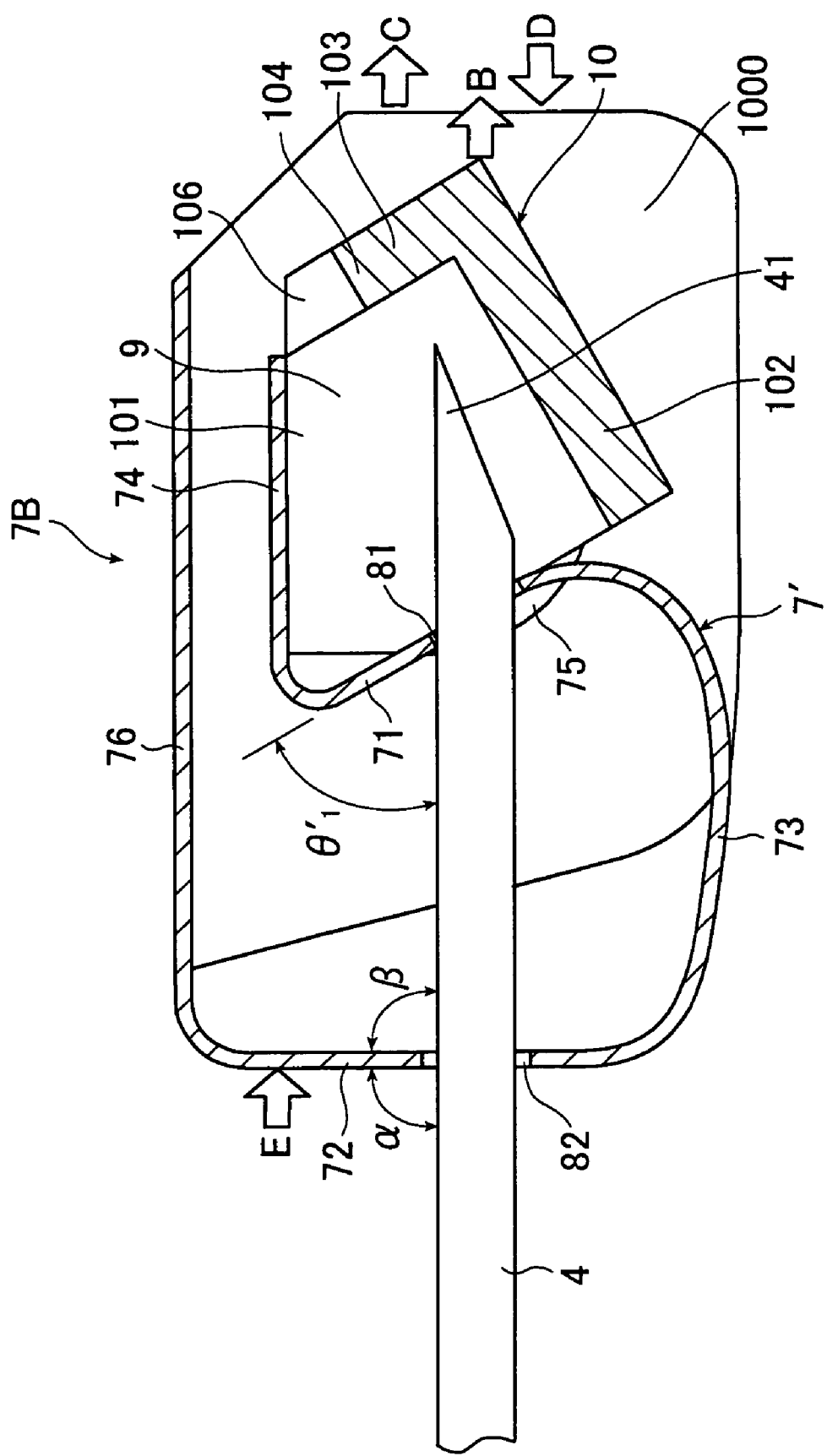
FIG. 11 is a cross-sectional side view showing a state where a protector according to a fifth embodiment of the present invention is fitted to the needle body, in which the protector is shown as being in the second attitude.

FIG. 11 is a cross-sectional side view showing a protector according to a fifth embodiment of the present invention, in which the protector is shown as being in the second attitude.

Hereinbelow, the fifth embodiment of the protector of the present invention will be described with reference to the above figure. The description will be focused on differences from the fourth embodiment described above, and description of matters identical to those of the fourth embodiment will be omitted.

A protector 7B of this embodiment is the same as that of the fourth embodiment described above except that it has cover portions 1000, 1000 for covering the plastic member 10 (the area near the needle-body abutting portion 104).

The cover portions 1000, 1000 are provided so as to extend in the direction toward the other end (downward direction in FIG. 10) from both side portions of a sixth area 76 and are arranged substantially perpendicular to the first area 71, the second area 72 etc, the sixth area 76 being provided so as to extend in the tip end direction from one end portion of the second area 72. That is, both the cover portions 1000, 1000 are provided substantially parallel to each other.

That is, as seen from the front, the sixth area 76 and the cover portions 1000, 1000 are substantially C-shaped as a whole.

The cover portions 1000, 1000 each covers the first area 71, the fourth area 74, the fifth area 75, and the plastic member 10 from the side.

Each of such cover portions 1000, 1000 functions to hinder the operation of moving the area near the needle-body abutting portion 104 in the tip end direction in the second attitude.

That is, even when attempting to apply such a pulling force as indicated by the arrow B in FIG. 11 onto the tip end portion (area near the needle-body abutting portion 104) of the plastic member 10 with a finger or the like, the tip end portion of the plastic member 10 cannot be touched with the finger or the like since it is covered from the side by each of the cover portions 1000, 1000, thus making it impossible to perform such an operation.

Unlike the above arrangement, if it is possible to apply the above-mentioned pulling force B onto the tip end portion of the plastic member 10, this pulling force B is transmitted by way of the fourth area 74 to the first area 71, where it acts to make the first-area inclination angle $\theta_1'$ become larger. As a result, the frictional force between the inner surface of the first hole 81 and the surface of the needle tube 4 (the braking force acting on the protector 7B) decreases, which may cause the protector 7B to dislodge (drop out) from the needle tube 4.

In contrast, in the protector 7B, the cover portions 1000, 1000 are provided as described above, so that the operation of applying an external force such as the above-mentioned pulling force B is hindered, which advantageously makes it possible to prevent the protector 7B from being dislodged as described above. Therefore, the separation of the protector 7B from the needle tube 4 can be prevented even when intentionally attempting to dislodge it from the needle tube 4, thus ensuring a particularly high level of safety.

Further, the protector 7B described above has means for applying such a force as to make the inclination angle of the second area 72 (plate-like member near the second hole 82) relative to the above-mentioned needle tube 4 become smaller when an external force acting in the base end direction or the tip end direction is exerted on each of the cover portions 1000, 1000 in the second attitude.

That is, when an external force acting in the tip end direction is exerted on the cover portions 1000, 1000 by applying such a pulling force as indicated by the arrow C in FIG. 11 to the tip end portion of each of the cover portions 1000, 1000, for example, this pulling force C is transmitted by way of the sixth area 76 to the second area 72, where it acts to make the inclination angle of the second area 72 relative to the needle tube 4 (the angle indicated by β in FIG. 11) become smaller.

As a result, a frictional force (a braking force acting on the protector 7B) is generated or increased between the inner surface of the second hole 82 and the surface of the needle tube 4 to resist the pulling force C. That is, in addition to the first area 71, the second area 72 also exerts a braking action with respect to the needle tube 4, thereby more reliably prohibiting (inhibiting) the movement of the protector 7B. Note that, in a likewise manner, when such a pressing force as indicated by the arrow E in FIG. 11 is applied to the base end portion of the protector 7B, the force acts to make the inclination angle β of the second area 72 relative to the needle tube 4 become smaller.

Further, the above-mentioned pulling force C is transmitted to the first area 71 from the second area 72 by way of the third area 73, so that it also acts to make the first-area inclination angle $\theta_1'$ become further smaller.

Note that, the above-mentioned inclination angles α, β can be adjusted in an arbitrary manner by selecting the size of the second hole 82 as appropriate.

As described in the foregoing, according to this embodiment, it is possible to more reliably prevent the protector 7B from being dislodged from the needle tube 4 even if an external force acting in the tip end direction is exerted on the cover portions 1000, 1000.

Note that, it is sufficient that the cover portions 1000, 1000 cover at least an area near the needle-body abutting portion 104.

Embodiment of Indwelling Needle Assembly

Figure 12:
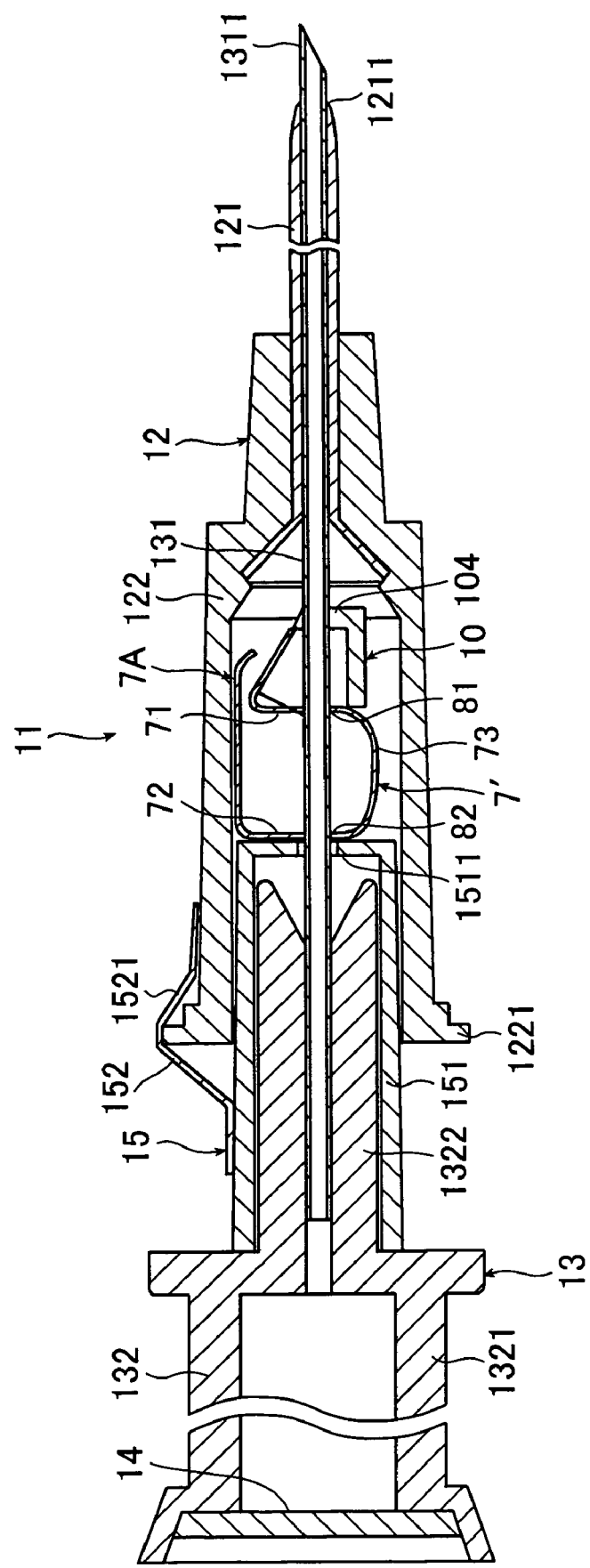
FIG. 12 is a longitudinal sectional view showing an embodiment of an indwelling needle assembly (assembled state) of the present invention.
Figure 13:
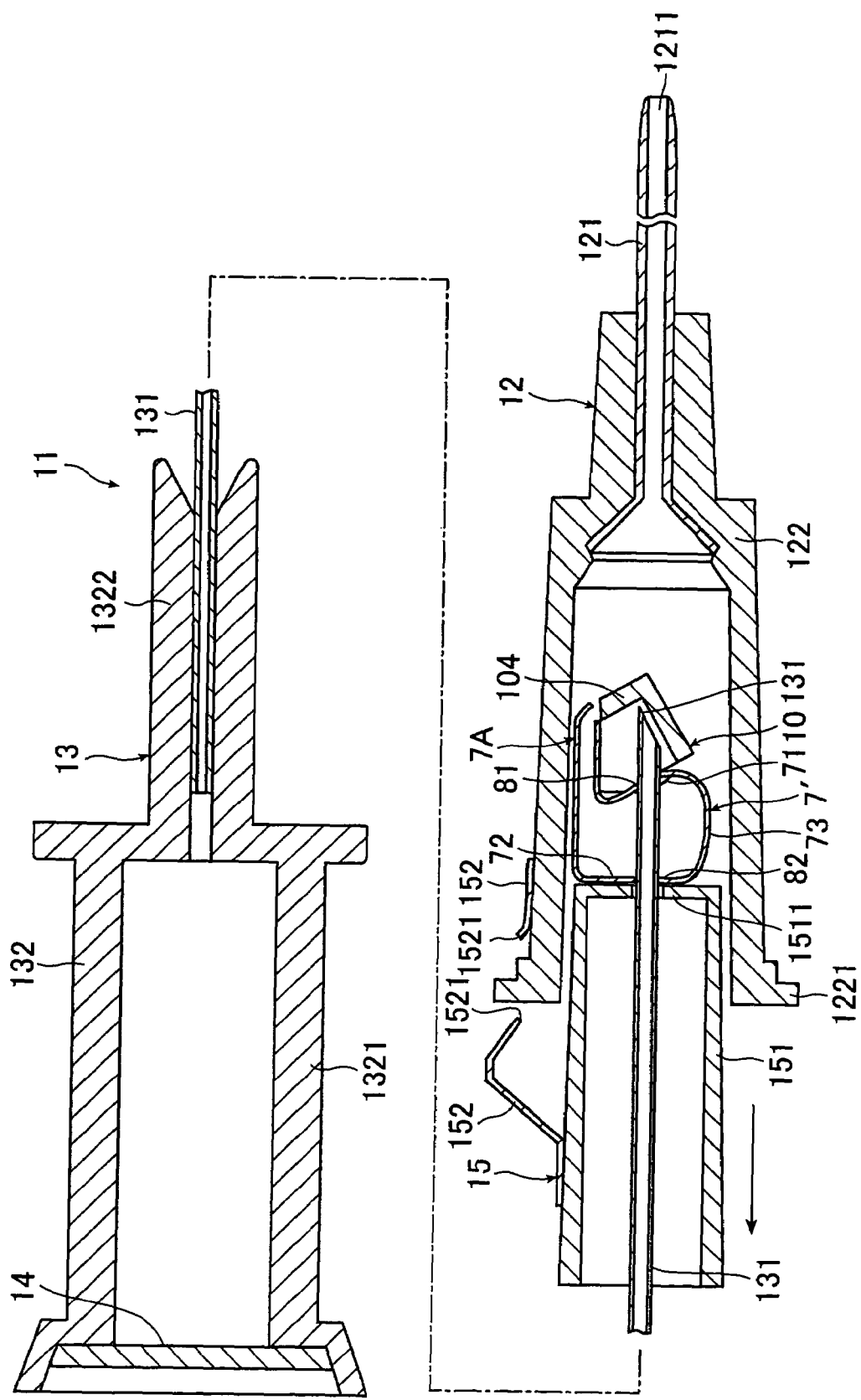
FIG. 13 is a longitudinal sectional view showing a state where an inner needle hub is moved relative to an outer needle hub in the base end direction in the indwelling needle assembly shown in FIG. 12.

FIGS. 12 and 13 are each a longitudinal sectional view of an embodiment of an indwelling needle assembly of the present invention. Note that, in the following description, the needle tip side as seen in FIGS. 12 and 13 is referred to as a "tip end", whereas the hub side is referred to as a "base end". Also, with the tip end being pointed up, the left-hand side is referred to as "one end", whereas the right-hand side is referred to as "the other end".

Hereinbelow, the embodiment of the indwelling needle assembly of the present invention will be described with reference to those figures. The description will be focused on differences from the aforementioned embodiments of the protector, and description of matters identical to those of the aforementioned embodiments will be omitted.

An indwelling needle assembly 11 shown in each of those figures is provided with an outer needle and an inner needle, which is used in particular to constitute an indwelling needle assembly for infusion and is provided with: an outer needle with hub 12 which is composed of an outer needle 121 serving as an indwelling needle and an outer needle hub 122 provided on the base end side of the outer needle 121; an inner needle with hub 13 which is composed of an inner needle 131 to be inserted into the outer needle 121 and an inner hub 132 provided on the base end side of the inner needle 131; and the protector 7A of the fourth embodiment described above which is fitted to the inner needle 131. Hereinbelow, the constructions of the respective portions will be described.

The outer needle 121 used is preferably hollow and has some degree of flexibility. Although the constituent material for the outer needle 121 is not particularly limited, various kinds of soft resin such as ethylene-tetrafluoroethylene copolymer (ETFE), polyurethane, or polyether nylon resin are preferably used.

For easy, low-invasive puncture into a living body, the tip end portion of the outer needle 121 is tapered such that the outer diameter thereof gradually decreases toward its tip end.

The outer needle hub 122 is secured in a liquid-tight manner to the base end of the outer needle 121, so that the inner hole of the outer needle 121 is communicated with the inner portion of the outer needle hub 122. The outer needle hub 122 is a substantially tubular member which is tapered such that its outer diameter and inner diameter gradually increase toward the base end.

The material, shape etc of the inner needle (needle body) 131 are the same as those of the needle tube 4 according to the first embodiment described above.

This inner needle 131 is used in a state where it is inserted into the inner hole of the outer needle 121, that is, in the state shown in FIG. 12. Hereinafter, this state will be referred to as the "assembled state".

The length of the inner needle 131 is set to such a length that at least allows a needle tip 1311 to project from a tip-end opening 1211 of the outer needle 121 in the assembled state.

The base end portion of the inner needle 131 is secured to the tip end portion of the inner needle hub 132 so that the inner hole of the inner needle 131 is communicated with the interior space of the inner needle hub 132.

The inner needle hub 132 is constructed of a substantially cylindrical hollow member, which has a main body portion 1321 and a narrow-diameter portion 1322 that is provided on the tip end side of the main body portion 1321 and is narrower in diameter than the main body portion 1321.

The inner needle hub 132 is preferably formed of a transparent (uncolored transparent), colored transparent, or semi-transparent resin to ensure the visibility of its inner portion. This allows a flashback of blood flowing in through the inner needle 131 to be visually confirmed when the needle tip 1311 has secured the blood vessel.

Also, an air filter 14 that is permeable to gas but blocks liquid is placed over the opening of the base end portion of the inner hub 132 so as to cover the opening.

The constituent materials for the outer needle hub 122 and the inner needle hub 132 are not particularly limited, and various kinds of resin materials may be used.

The protector 7A is fitted to the inner needle 131, and as shown in FIG. 12, it is accommodated within the interior space of the outer needle hub 122 in the assembled state.

The indwelling needle assembly 11 of this embodiment has connecting means 15 for connecting the protector 7A and the outer needle hub 122 with each other in the assembled state. This connecting means 15 has a cylinder member (abutting member) 151 having a cylindrical shape and a tape 152 for connecting the cylinder member 151 and the outer needle hub 122 with each other.

The cylinder member 151 has a base-end opening. In the assembled state, the narrow-diameter portion 1322 of the inner needle hub 132 is inserted through the base-end opening into the inside of the cylinder member 151 for a loose fit therewith.

A tip end wall (bottom portion) 1511 is provided at the tip end portion of the cylinder member 151. A hole is formed in the center of the tip end wall 1511, and the inner needle 131 penetrates through the hole.

In the assembled state, a part of the cylinder member 151 on the tip end side is inserted into the inside of the outer needle hub 122 for a loose fit therewith. Also, in the assembled state, the tip end portion (the outer surface of the tip end wall 1511) of the cylinder member 151 is in abutment with or in close proximity to the base end portion of the protector 7A.

The tape 152 is a sheet-like member having flexibility, which is formed of, for example, polyethylene, polypropylen, polyester, paper, non-woven fabric etc. The base end portion thereof is heat-sealed or adhered onto an outer surface of the cylinder member 151 whereas the tip end portion thereof is heat-sealed or adhered onto an outer surface of the outer needle hub 122. That is, the tape 152 is provided so as to straddle a flange 1221 provided on the outer periphery of the base end of the outer needle hub 122.

A perforation 1521 is formed across the tape 152 as a rupturing portion which ruptures upon separation of the protector 7A and the outer needle hub 122 from each other.

Due to the above arrangement, in the assembled state, the outer needle hub 122 and the protector 7A are connected with each other through the connecting means 15.

Due to the provision of such connecting means 15, when the inner needle with hub 13 is moved in the base end direction relative to the outer needle with hub 12 from the assembled state of the indwelling needle assembly 11 (when the inner needle 131 of the inner needle with hub 13 is pulled out from the outer needle 121 of the outer needle with hub 12), the protector 7A abuts with the tip end portion of the cylinder member 151 so that its movement in the base end direction is prevented and thus it remains on the outer needle with hub 12 side. That is, with respect to the inner needle 131, the protector 7A makes relative movement in the tip end direction while maintaining the first attitude, and when the needle tip 1311 of the inner needle 131 passes the needle-body abutting portion 104, the protector 7A is displaced into the second attitude in which it covers the needle tip 1311 of the inner needle 131.

As described above, once in the second attitude, the protector 7A is prohibited (inhibited) from making relative movement with respect to the inner needle 131. Therefore, when the inner needle with hub 13 is further moved in the base end direction relative to the outer needle with hub 12 from the state where the protector 7A has assumed the second attitude, the resulting operational force (pulling-out force) acts on the tape 152 via the cylinder member 151, which results in rupturing of the perforation 1521. As a result, the protector 7A is separated apart from the outer needle with hub 12 (outer needle hub 122) to remain on the tip end of the inner needle 131, thereby guarding (covering) the needle tip 1311 thereof.

As described above, in the indwelling needle assembly 11, it is possible to cover the needle tip 1311 of the inner needle 131 with the protector 7 as well as to detach the protector 7A from the outer needle with hub 12 by only performing the operation of moving the inner needle with hub 13 in the base end direction relative to the outer needle with hub 12, so that it is unnecessary to perform a separate operation for covering the needle tip 1311 of the inner needle 131 with the protector 7A. As a result, the needle tip 1311 of the inner needle 131 can be covered with (accommodated into) the protector 7A in an extremely easy and reliable manner.

Next, an example method of using the indwelling needle assembly 11 will be described in detail.

[1] The indwelling needle assembly 11 is set to the assembled state, and while grasping the inner needle hub 132 etc with a hand, the inner needle 131 and the outer needle 121 are punctured into the blood vessel (vein or artery) of a patient.

[2] Once the needle tip 1311 of the inner needle 131 is punctured into the blood vessel, due to the internal pressure of the blood vessel (blood pressure), the blood flows backward within the inner needle 131 in the base end direction to be introduced into the inner needle hub 132, and this flashback can be visually confirmed through the inner needle hub 132 that has visibility. As a result, it is possible to learn that the needle tip 1311 of the inner needle 131 has secured the blood vessel.

Note that, following this inflow of blood, while air within the inner needle hub 132 is discharged through the air filter 14, blood cannot pass through the air filter 14, so that there is no leakage of the blood to the exterior.

[3] When the inner needle 131 and the outer needle 121 are further advanced in the tip end direction by a minute distance, the tip-end opening 1211 of the outer needle 121 is inserted into the blood vessel. This allows the outer needle 121 to secure the blood vessel.

[4] While using one hand to hold the outer needle 121 indwelled in the blood vessel, the inner needle hub 132 is grasped by the other hand to pull it in the base end direction. This allows the inner needle 131 to be drawn out from the outer needle 121. At this time, the protector 7A is connected with the outer needle hub 122, so that it remains on the outer needle with hub 12 side. That is, the protector 7A moves in the tip end direction relative to the inner needle 131.

According to the present invention, the protector 7A can move smoothly relative to the needle tube 4 as described above, so that the inner needle 131 can be drawn out from the outer needle 121 with only a small operational force, thus allowing this operation to be performed easily and swiftly. Further, it is also possible to prevent such a problem that the connection effected by the connecting means 15 is released (the perforation 1521 is ruptured) before the protector 7A is brought into the second attitude.

[5] When the inner needle hub 132 is further pulled in the base end direction, as described above, the needle tip 1311 of the inner needle 131 passes the needle-body abutting portion 104, so that the braking-action reserving state effected by the needle-body abutting portion 104 is released. As a result, the protector 7A is deformed elastically (due to its own elasticity) into the second attitude shown in FIG. 13.

Once the protector 7A is brought into the second attitude, due to the braking action of the first area 71, the protector 7A is stopped (becomes stationary) with respect to the inner needle 131 before the needle tip 1311 passes the first hole 81. As a result, the movement of the protector 7A along the longitudinal direction of the inner needle 131 is prohibited (inhibited), allowing the protector 7A to maintain the state where it covers (accommodates) the needle tip 1311 of the inner needle 131.

[6] When the inner needle hub 132 is further pulled in the base end direction from the state where the protector 7A has assumed the second attitude, the pulling force acts on the connecting means 15 so that the perforation 1521 is ruptured. As a result, the protector 7A is separated apart from the outer needle with hub 12 (outer needle hub 122) to remain on the tip end of the inner needle 131 (see FIG. 13).

[7] A connector etc (not shown) of an infusion set is quickly connected to the outer needle hub 122 of the outer needle with hub 12 from which the inner needle 131 is drawn out, and administration of infusion is commenced according to a prescribed method.

After the inner needle 131 is thus drawn out from the outer needle 121, the inner needle with hub 13 becomes unnecessary, so that it is discarded for disposal.

As has been described in the foregoing, according to the indwelling needle assembly 11, the needle tip 1311 of the inner needle with hub 13 drawn out from the outer needle with hub 12 is accommodated into the protector 7A, with the result that, in particular, the needle tip 1311 does not project through the tip end of the protector 7A or the protector 7A is not dislodged from the inner needle 131, thereby preventing accidental sticking of the needle tip 1311 into a hand, finger, or the like of a person performing needle disposal etc.

Figure 14:
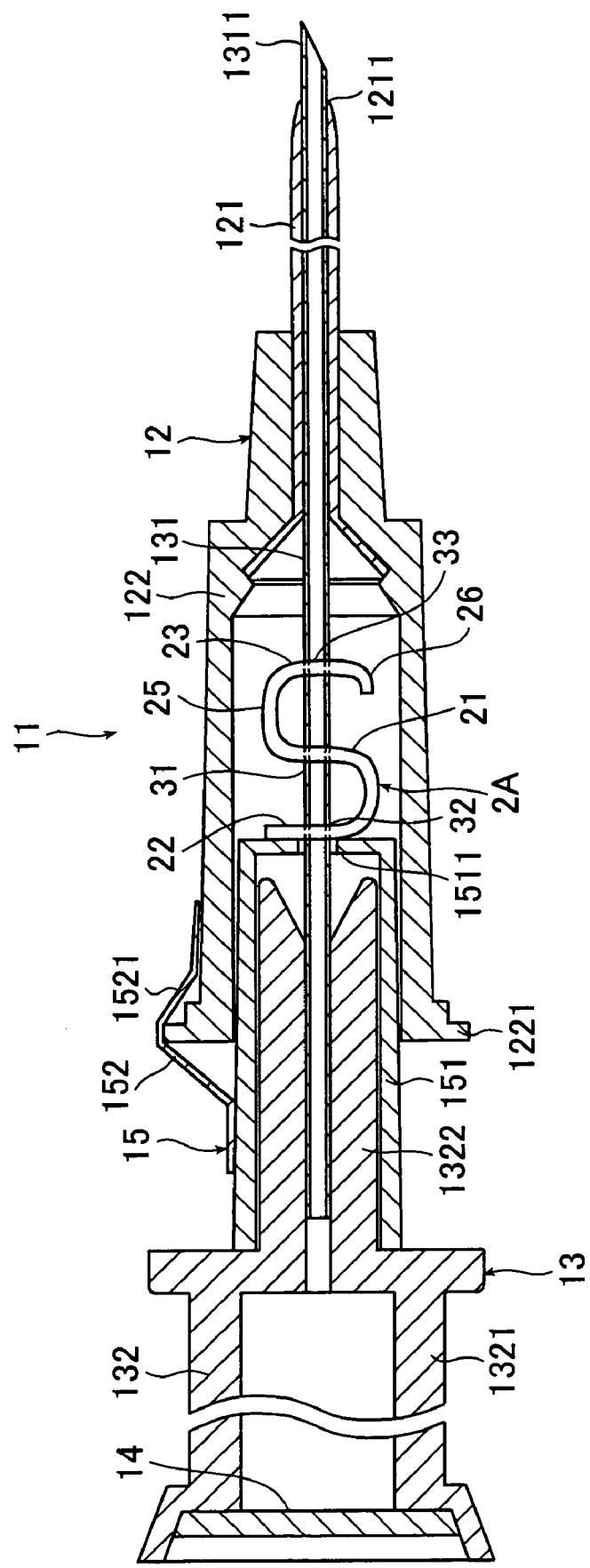
FIG. 14 is a longitudinal sectional view of an embodiment of an indwelling assembly of the present invention, showing another construction example of the protector.

FIG. 14 is a view showing another construction example of the protector in which the protector 2A of the first embodiment described above is used instead of the protector 7A of FIG. 12. In this way, the indwelling needle assembly 11 may also be provided with the protector of each of the above-described first through third embodiments and the fifth embodiment.

Figure 15:
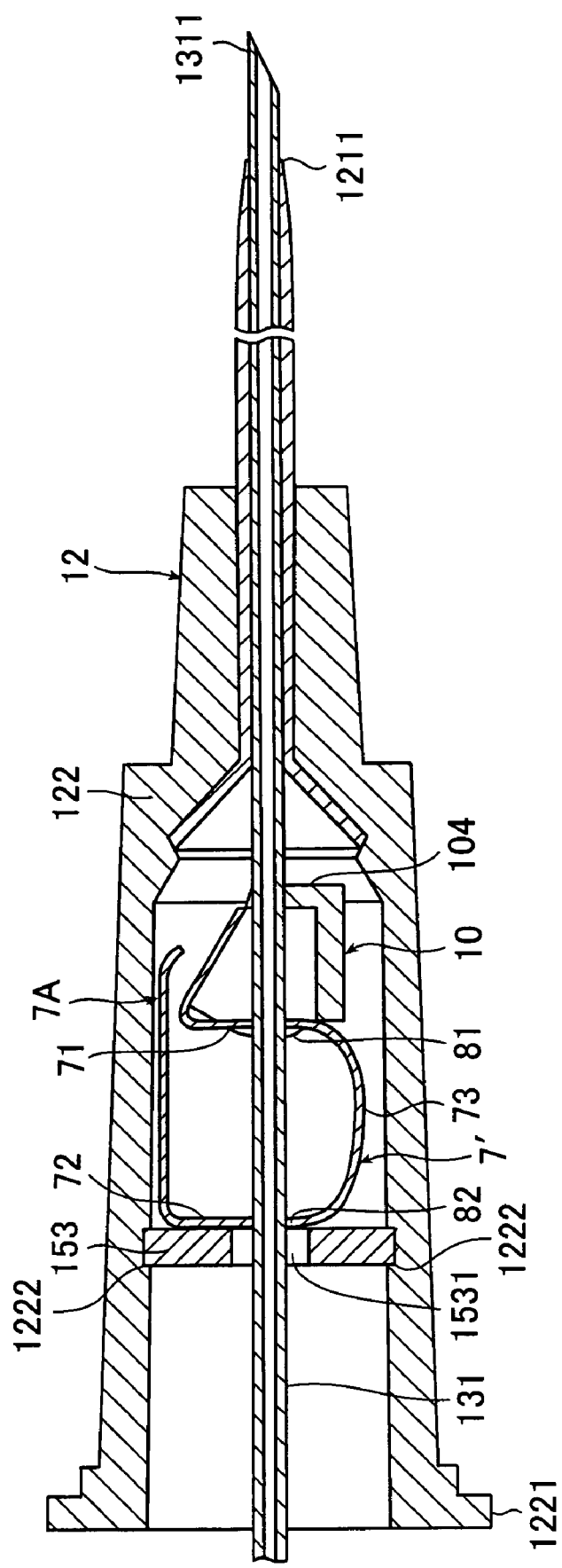
FIG. 15 is a longitudinal sectional view of the vicinity of the outer needle hub in the assembled state, showing another construction example of connecting means.

FIG. 15 is a view showing another construction example of the connecting means, which is a longitudinal sectional view of the outer needle hub and its vicinity in the assembled state.

Hereinbelow, while another construction example of the connecting means in the indwelling needle assembly of the present invention will be described with reference to the same figure, the description will be focused on differences from the aforementioned embodiments, and description of matters identical to those of the aforementioned embodiments will be omitted.

The connecting means in the indwelling needle assembly of this embodiment is a ring member 153 of an annular (disk) shape or a substantially C shape which has a hole 1531 through which the inner needle 131 is penetrated (inserted).

In the assembled state, the outer peripheral portion of this ring member 153 is inserted (locked) into a concave portion 1222 (groove portion) formed in the inside of the outer needle hub 122, and the tip end face of the ring member 153 is in abutment with or in close proximity to the base end portion of the protector 7A. Further, the ring member 153 also functions as an abutting member that may abuts with the protector 7A from the base end side.

When the inner needle with hub 13 is moved in the base end direction relative to the outer needle with hub 12 from the above assembled state, the protector 7A abuts with the tip end face of the ring member 153 so that its movement in the base end direction is prevented and thus it remains on the outer needle with hub 12 side. That is, with respect to the inner needle 131, the protector 7A makes relative movement in the tip end direction while maintaining the first attitude, and when the needle tip 1311 of the inner needle 131 passes the needle-body abutting portion 104, the protector 7A is displaced into the second attitude in which it covers the needle tip 1311 of the inner needle 131.

When the inner needle with hub 13 is further moved in the base end direction relative to the outer needle with hub 12 from the above state, due to the resulting operational force (pulling-out force), the ring member 153 is deformed in such a way that its apparent outer diameter becomes smaller, with the result that it is dislodged from the concave portion 1222 to move in the base end direction relative to the outer needle hub 122. Due to this movement, the locking of the ring member 153 to the outer needle hub 122 is released, so that the protector 7A is separated apart from the outer needle hub 122 to remain on the tip end of the inner needle 131, thereby guarding the needle tip 1311 thereof.

In the foregoing, the protector and the indwelling needle assembly of the present invention have been described based on the embodiments thereof shown in the drawings. However, the present invention is not limited to the above-described embodiments, and the respective portions constituting the protector and the indwelling needle assembly may be replaced by those constructed in any given manner so as to be able to exert the same functions.

For instance, the main body portion of the protector according to each of the first through third embodiments described above does not need to be substantially S-shaped as a whole and it may also be substantially "e"-shaped as a whole, for example.

Further, in the protector according to each of the above-described first through third embodiments as well, the main body portion of the protector may be constructed of plural parts. For example, the plate-like brake portion and the urging member (spring), which urges the brake portion in such a way that the inclination angle thereof relative to the needle body becomes smaller, may be constructed of separate parts.

Further, the protector of the present invention is not only used for various injection needles but also may be used by being fitted to an indwelling needle assembly in which an indwelling needle (outer needle) is used in combination therewith.

Further, the construction of the connecting means in the indwelling needle assembly of the present invention is not limited to the one shown in the drawings but any connecting means may be employed as long as it is capable of keeping the connected state between the protector and the outer needle hub until the protector is displaced (deformed) from the first attitude into the second attitude. Further, such connecting means may not be provided.

The invention claimed is:

1. A protector displaceable between a first position in which said protector can move relatively along a longitudinal direction of a needle body having a sharp needle tip at a tip end and a second position in which the relative movement of said protector along the longitudinal direction of said needle body is prohibited in a state where said protector covers the needle tip of said needle body, said protector comprising a main body portion formed by deforming a plate-like member having an elasticity, said main body portion comprising:
    a first area formed in a center thereof, in which a first hole through which said needle body can penetrate is formed;
    a second area formed on a needle root side thereof, in which a second hole through which said needle body can penetrate is formed;
    a third area formed on the needle tip side thereof, in which a penetration portion through which said needle body can penetrate is formed; and
    a rear connection portion connecting respective end portions of said first area and said second area with each other and a front connection portion connecting respective end portions of said first area and said third area with each other, said main body portion thus having a substantially S shape as a whole
    a connection portion between said first area and said rear connection portion is urged in such a direction as to make an angle formed between said first area and said rear connection portion become smaller;
    in said first position, said needle body penetrates through said first hole, said second hole, and said penetration portion; and
    by moving said protector in a tip end direction relative to said needle body to release an engagement between said penetration portion and said needle body, the angle formed between said first area and said rear connection portion becomes smaller to cause said protector to be elastically deformed into said second position such that an inclination angle of said first area relative to said needle body becomes smaller than the inclination angle in said first position, so that a frictional force is generated or increased between an inner surface of said first hole and an outer peripheral surface of said needle body to thereby prohibit the relative movement of said protector along the longitudinal direction of said needle body.

2. The protector according to claim 1, comprising a cap member which is located between said penetration portion and said first hole and covers the needle tip of said needle body in said second position.

3. The protector according to claim 1, comprising a needle-tip receiving portion that covers said needle tip from the tip end side.

4. A protector displaceable between a first position in which said protector can move relatively along a longitudinal direction of a needle body having a sharp needle tip at a tip end and a second position in which the relative movement of said protector along the longitudinal direction of said needle body is prohibited in a state where said protector covers the needle tip of said needle body, said protector being formed by deforming a plate-like body constructed of a metallic material, comprising:
    a protector main body which has: a first area in which a first hole through which said needle body can penetrate is formed; a second area formed on a needle root side thereof in which a second hole through which said needle body can penetrate is formed; and a third area connecting respective end portions of said first area and said second area with each other, said first area , said second area and said third area of said main body portion having a substantially C shape as a whole;
    urging means for urging said first area so that an angle formed between said first area and said third area in a connection portion between said first area and said third area becomes smaller to thereby make an inclination angle of said first area relative to said needle body become smaller; and
    a needle-body abutting portion constructed of a resin material, which is provided further on the needle tip side than said first area to abut said needle body in said first position to prevent the inclination angle of said first area relative to said needle body from changing,
    in said first position, said needle body penetrates through said first hole and said second hole; and
    when said protector is moved in a tip end direction from said first position relative to said needle body and said needle-body abutting portion passes said needle tip to be separated apart from said needle body, the angle formed between said first area and said third area becomes smaller due to said urging means to cause said protector to be deformed into said second position such that the inclination angle of said first area relative to said needle body becomes smaller than the inclination angle in said first position, so that a frictional force is generated or increased between an inner surface of said hole and a surface of said needle body to thereby prohibit the relative movement of said protector along the longitudinal direction of said needle body.

5. The protector according to claim 4, comprising a needle-tip receiving portion that covers said needle tip from the tip end side in said second position.

6. An indwelling needle assembly characterized by comprising:
    an inner needle having a sharp needle tip at a tip end; said protector according to claim 1 which is fitted to said inner needle;
    an inner needle hub installed on the base end side of said inner needle;
    a hollow outer needle into which said inner needle can be inserted; and
    an outer needle hub installed on the base end side of said outer needle.

7. An indwelling needle assembly comprising:

an inner needle having a sharp needle tip at a tip end;

said protector according to claim 4 which is fitted to said inner needle;

an inner needle hub installed on a base end side of said inner needle;

a hollow outer needle into which said inner needle can be inserted; and an outer needle hub installed on the base end side of said outer needle.

* * * * *